United States Patent
Willms et al.

(10) Patent No.: US 7,141,531 B2
(45) Date of Patent: Nov. 28, 2006

(54) COMBINATIONS OF PHENYLSULFONYLUREA HERBICIDES AND SAFENERS

(75) Inventors: Lothar Willms, Hofheim (DE); Hermann Bieringer, Eppstein (DE); Erwin Hacker, Hochheim (DE); Gerhard Schnabel, Grosswallstadt (DE); Klaus Lorenz, Weiterstadt (DE)

(73) Assignee: Hoechst Schering AgrEvo GmbH, Berlin (DE)

(*) Notice: Subject to any disclaimer, the term of this patent is extended or adjusted under 35 U.S.C. 154(b) by 13 days.

(21) Appl. No.: 10/464,906

(22) Filed: Jun. 19, 2003

(65) Prior Publication Data

US 2004/0157737 A1    Aug. 12, 2004

Related U.S. Application Data

(63) Continuation of application No. 08/556,180, filed on Nov. 9, 1995, now abandoned.

(30) Foreign Application Priority Data

Nov. 11, 1994  (DE) ............................... P 44 40 354

(51) Int. Cl.
| A01N 25/32 | (2006.01) |
| A01N 43/26 | (2006.01) |
| A01N 43/56 | (2006.01) |
| A01N 43/00 | (2006.01) |
| A01N 43/42 | (2006.01) |
| A01N 43/66 | (2006.01) |

(52) U.S. Cl. ............... 504/106; 504/104; 504/108; 504/129; 504/136; 504/139; 504/140

(58) Field of Classification Search ............... 504/107, 504/133, 136, 104, 108, 129, 139, 140, 106
See application file for complete search history.

(56) References Cited

U.S. PATENT DOCUMENTS

| 4,623,727 A | 11/1986 | Hubele ............... 546/178 |
| 4,758,264 A | 7/1988 | Hubele ............... 504/105 |
| 4,785,105 A | 11/1988 | Hubele ............... 546/178 |
| 4,785,106 A | 11/1988 | Hubele ............... 546/178 |
| 4,822,884 A | 4/1989 | Hubele ............... 546/177 |
| 4,851,033 A | 7/1989 | Hubele ............... 504/105 |
| 4,881,966 A | 11/1989 | Nyffeler et al. |
| 4,891,057 A | 1/1990 | Sohn et al. |
| 4,902,340 A | 2/1990 | Hubele |
| 5,045,107 A | 9/1991 | Hubele ............... 504/105 |
| 5,449,812 A | 9/1995 | Schnabel et al. |
| 5,488,027 A * | 1/1996 | Bauer et al. ............... 504/105 |
| 5,648,315 A * | 7/1997 | Lorenz et al. ............... 504/214 |
| 5,696,053 A | 12/1997 | Schnabel et al. ............... 504/214 |
| 5,700,758 A | 12/1997 | Rösch et al. ............... 504/106 |
| 5,747,421 A | 5/1998 | Schnabel et al. ............... 504/214 |
| 5,922,646 A | 7/1999 | Schnabel et al. ............... 504/214 |
| 6,498,253 B1 | 12/2002 | Schnabel et al. ............... 544/321 |
| 6,569,805 B1 * | 5/2003 | Krahmer et al. ............... 504/103 |
| 6,683,027 B1 * | 1/2004 | Baltruschat et al. ............... 504/128 |

FOREIGN PATENT DOCUMENTS

| AU | A-34951/89 | 11/1989 |
| EP | 0 094 349 | 11/1983 |
| EP | 0 174 562 | 1/1987 |
| EP | 0 191 736 | 1/1988 |
| EP | 0 333 131 | 9/1989 |
| EP | 0 346 620 | 12/1989 |
| EP | 0 269 806 | 2/1991 |
| EP | 0 492 366 | 7/1992 |
| EP | 0 582 198 | 2/1994 |
| WO | WO 91/08202 | 6/1991 |
| WO | WO 94/06778 | 3/1994 |
| WO | WO 94/10154 | 5/1994 |
| WO | WO 95/07897 | 3/1995 |
| WO | WO 95/10507 | 4/1995 |
| ZA | 89/1960 | 3/1989 |
| ZA | 94/7120 | 6/1995 |

* cited by examiner

*Primary Examiner*—John Pak
(74) *Attorney, Agent, or Firm*—Frommer Lawrence & Haug LLP

(57) ABSTRACT

The invention relates to combinations of sulfonylurea herbicides (A) and their salts

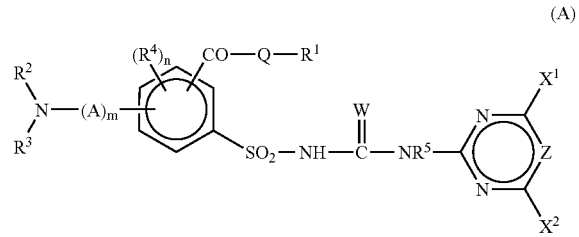

(A)

in which $R^2$ is H, OH, aliphatic hydrocarbon radical or hydrocarbon-oxy radical, and $R^1$ is an acyl radical, and the other symbols are as defined in claim 1, and safeners of type (B1) and (B2)

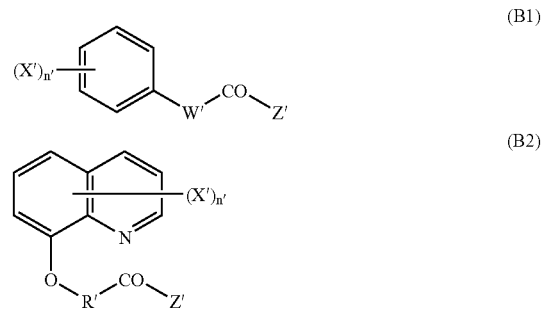

in which the symbols are as defined in claim 1.

17 Claims, No Drawings

COMBINATIONS OF PHENYLSULFONYLUREA HERBICIDES AND SAFENERS

This application is a Continuation of application Ser. No. 08/556,180, filed on Nov. 9, 1995, now abandoned.

The invention to the technical area of crop protection agents, in particular active substance/antidote combinations (=active substance/safener combinations) which are outstandingly suitable for use to combat competing harmful plants in crops of useful plants.

Some of the newer herbicidal active substances have very good properties on use and can be used with very low application rates to combat a wide spectrum of grassy and broad-leaved weeds.

However, many of the very effective active substances are not entirely compatible with (i.e. not sufficiently selective in) some important crop plants such as corn, rice or cereals, so that there are narrow limits on their use. Thus, in some crops they cannot be used at all or can be used only with such low application rates that the desired wide herbicidal activity on harmful plants is not ensured. Specifically, many herbicides of formula (A), which is defined hereinafter, cannot be used completely selectively to combat harmful plants in corn, rice, cereals or some other crops.

Some of our recent experimental work has now shown that crop plants such as corn, rice, wheat, barley and others can, surprisingly, be protected from unwanted damage by said herbicides when they are applied together with certain compounds which act as herbicide antidotes or safeners.

The invention therefore relates to herbicide/safener combinations, for example in the form of herbicidal compositions, containing A) at least one herbicidal active substance from the group of substituted phenylsulfonylureas of the formula (A) and salts thereof

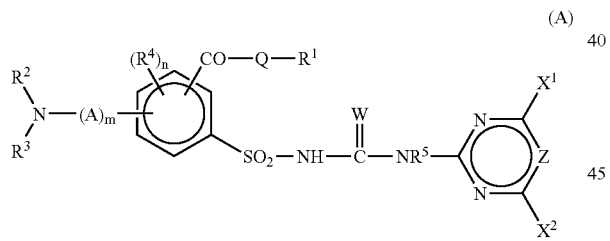

(A)

in which
W is O or S, preferably O,
A is a group of the formula CR'R", in which R' and R" are, independently of one another, H or $(C_1-C_4)$alkyl,
Q is O, S or a group $NR^6$,
m is 0 or 1,
n is 0, 1, 2 or 3,
$R^1$ is H, a hydrocarbon radical or a heterocyclic radical, each of the two last-mentioned radicals being unsubstituted or substituted,
$R^2$ is H, OH or an aliphatic hydrocarbon or hydrocarbonoxy radical, each of the two last-mentioned radicals being unsubstituted or substituted,
$R^3$ is an acyl radical,
$R^4$ is halogen, CN, $NO_2$, $(C_1-C_4)$alkyl, $(C_1-C_4)$-alkoxy, $[(C_1-C_4)$alkyl]carbonyl, $[(C_1-C_4)$-alkoxy]carbonyl, each of the four last-mentioned radicals being unsubstituted or substituted,
$R^5$ is H, $(C_1-C_5)$alkyl or $(C_1-C_4)$alkoxy,
$R^6$ is H, $(C_1-C_4)$alkyl, $(C_3-C_4)$alkenyl, $(C_3-C_4)$alkynyl, each of the three last-mentioned radicals being unsubstituted or substituted by one or more radicals from the group consisting of halogen, $(C_1-C_4)$alkyl, $(C_1-C_4)$alkoxy and $(C_1-C_4)$alkylthio, or is $(C_1-C_4)$alkoxy or OH,
$X^1$, $X^2$ are, independently of on another, H, halogen, $(C_1-C_6)$alkyl, $(C_2-C_6)$alkenyl, $(C_2-C_6)$alkynyl, $(C_3-C_7)$cycloalkyl, $(C_1-C_6)$alkoxy, $(C_2-C_6)$alkenyloxy, $(C_2-C_6)$alkynyloxy, $(C_1-C_6)$alkylthio, mono- or di-$[(C_1-C_4)$alkyl]amino, each of the ten last-mentioned radicals being unsubstituted or substituted by one or more radicals from the group consisting of halogen, $(C_1-C_4)$alkoxy, $(C_1-C_4)$haloalkoxy and $(C_1-C_4)$alkylthio, and
Z is CH, N or a group of the formula C—$R°$ in which $R°$ is halogen, cyano, $(C_1-C_3)$alkyl, $(C_1-C_3)$haloalkyl, $(C_1-C_3)$alkoxy or $(C_1-C_3)$haloalkoxy, and B) at least one safener from the group of compounds of the formulae (B1) and (B2)

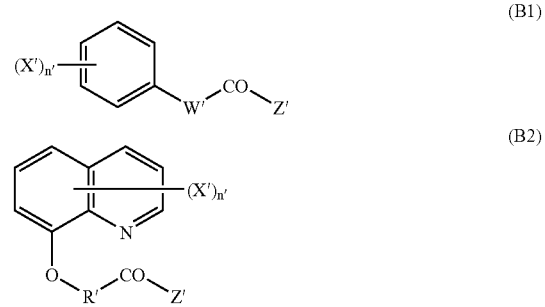

in which
X' is hydrogen, halogen, $(C_1-C_4)$alkyl, $(C_1-C_4)$alkoxy, nitro or $(C_1-C_4)$haloalkyl,
Z' is $OR^7$, $SR^7$ or $NR^7R^8$ or is a saturated or unsaturated 3- to 7-membered heterocycle which has at least one nitrogen atom and up to 3 hetero atoms, is linked via the nitrogen atom to the carbonyl group in (B1) or (B2) and is unsubstituted or substituted by radicals from the group consisting of $(C_1-C_4)$alkyl, $(C_1-C_4)$-alkoxy or optionally substituted phenyl, preferably a radical of the formula $OR^7$, $NHR^8$ or $N(CH_3)_2$, in particular of the formula $OR^7$,
R* is a ($C_1$ or $C_2$)alkanediyl chain which is unsubstituted or substituted by one or two $(C_1-C_4)$alkyl radicals or by $[(C_1-C_3)$alkoxy]-carbonyl,
$R^7$ is hydrogen or an unsubstituted or substituted aliphatic hydrocarbon radical, preferably having a total of 1 to 18 carbon atoms,
$R^8$ is hydrogen, $(C_1-C_6)$alkyl, $(C_1-C_6)$alkoxy or optionally substituted phenyl,
n' is an integer from 1 to 5, preferably 1 to 3,
W' is a divalent heterocyclic radical from the group of partially unsaturated or heteroaromatic 5-membered heterocycles having 1 to 3 ring hetero atoms of the type of N and O, the ring containing at least one nitrogen atom and at most one oxygen atom, preferably a radical from the group of radicals of the formulae (W1) to (W4),

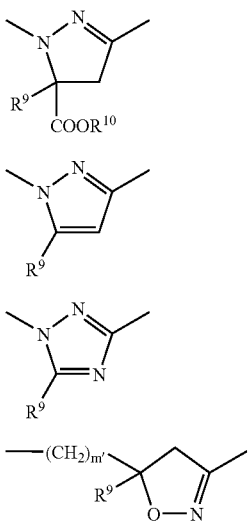

R$^9$ is hydrogen, (C$_1$–C$_8$)alkyl, (C$_1$–C$_8$)haloalkyl, (C$_3$–C$_{12}$)cycloalkyl or optionally substituted phenyl, R$^{10}$ is hydrogen, (C$_1$–C$_8$)alkyl, (C$_1$–C$_8$)haloalkyl, (C$_1$–C$_4$)alkoxy-(C$_1$–C$_4$)alkyl, (C$_1$–C$_6$)hydroxyalkyl, (C$_3$–C$_{12}$) cycloalkyl or tri-(C$_1$–C$_4$)alkylsilyl, and m' is 0 or 1.

Unless specifically defined otherwise, the following definitions apply to the radicals in the formulae (A), (B1) and (B2) and formulae hereinafter.

The radicals alkyl, alkoxy, haloalkyl, haloalkoxy, alkylamino and alkylthio, and the corresponding unsaturated and/or substituted radicals, can be straight-chain or branched in the carbon framework in each case. Unless specifically indicated, the lower carbon frameworks, e.g. with 1 to 6 carbon atoms, and in the case of unsaturated groups with 2 to 6 carbon atoms, are preferred for these radicals. Alkyl radicals, including in combined meanings such as alkoxy, haloalkyl etc., are, for example, methyl, ethyl, n- or i-propyl, n-, i-, t- or 2-butyl, pentyls, hexyls such as n-hexyl, i-hexyl and 1,3-dimethylbutyl, heptyls such as n-heptyl, 1-methylhexyl and 1,4-dimethylpentyl; alkenyl and alkynyl radicals have the meaning of the possible unsaturated radicals corresponding to the alkyl radicals; alkenyl is, for example, allyl, 1-methyl-2-propenyl, 2-methyl-2-propenyl, 2-butenyl, 3-butenyl, 1-methyl-3-butenyl and 1-methyl-2-butenyl; alkynyl is, for example, propargyl, 2-butynyl, 3-butynyl, 1-methyl-3-butynyl. "(C$_1$–C$_4$)alkyl" is the short way of writing alkyl having 1 to 4 carbon atoms; a corresponding statement applies to other general definitions of radicals with ranges indicated in brackets for the possible number of carbon atoms.

Halogen is, for example, fluorine, chlorine, bromine or iodine. Haloalkyl, -alkenyl and -alkynyl are alkyl, alkenyl and alkynyl, respectively, partly or completely substituted by halogen, preferably by fluorine, chlorine and/or bromine, in particular by fluorine or chlorine, for example CF$_3$, CHF$_2$, CH$_2$F, CF$_3$CF$_2$, CH$_2$FCHCl, CCl$_3$, CHCl$_2$, CH$_2$CH$_2$Cl; haloalkoxy is, for example, OCF$_3$, OCHF$_2$, OCH$_2$F, CF$_3$CF$_2$O, OCH$_2$CF$_3$ and OCH$_2$CH$_2$Cl; a corresponding statement applies to haloalkenyl and other radicals substituted by halogen.

A hydrocarbon radical is a straight-chain, branched or cyclic and saturated or unsaturated, aliphatic or aromatic hydrocarbon radical, for example alkyl, alkenyl, alkynyl, cycloalkyl, cycloalkenyl or aryl; in this connection, aryl is a mono- bi- or polycyclic aromatic system, for example phenyl, naphthyl, tetrahydronaphthyl, indenyl, indanyl, pentalenyl, fluorenyl and the like, preferably phenyl; a hydrocarbon radical is preferably alkyl, alkenyl or alkynyl having up to 12 carbon atoms or cycloalkyl having 3, 4, 5, 6 or 7 ring atoms or phenyl; a corresponding statement applies to a hydrocarbon radical in a hydrocarbon-oxy radical.

A heterocyclic radical or ring (heterocyclyl) can be saturated, unsaturated or heteroaromatic; it preferably contains one or more hetero units in the ring, preferably from the group consisting of N, O, S, SO, SO$_2$; it is preferably an aliphatic heterocyclyl radical having 3 to 7 ring atoms or a heteroaromatic radical having 5 or 6 ring atoms and contains 1, 2 or 3 hetero units. The heterocyclic radical can be, for example, a heteroaromatic radical or ring (heteroaryl) such as, for example, a mono-, bi- or polycyclic aromatic system in which at least 1 ring contains one or more hetero atoms, for example pyridyl, pyrimidinyl, pyridazinyl, pyrazinyl, thienyl, thiazolyl, oxazolyl, furyl, pyrrolyl, pyrazolyl and imidazolyl, or is a partially hydrogenated radical such as oxiranyl, pyrrolidyl, piperidyl, piperazinyl, dioxolanyl, morpholinyl, tetrahydrofuryl. Suitable substituents for a substituted heterocyclic radical are the substituents mentioned hereinafter plus, in addition, oxo. The oxo group may also occur on the ring hetero atoms which can exist in various oxidation states, for example N and S.

Substituted radicals, such as substituted hydrocarbon radicals, for example substituted alkyl, alkenyl, alkynyl, aryl, phenyl and benzyl, or substituted heterocyclyl or heteroaryl, are, for example, a substituted radical derived from the unsubstituted parent structure, where the substituents are, for example, one or more, preferably 1, 2 or 3, radicals from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylamino-carbonyl, substituted amino such as acylamino, mono- and dialkylamino, and alkylsulfinyl, haloalkylsulfinyl, alkylsulfonyl, haloalkylsulfonyl and, in the case of cyclic radicals, also alkyl and haloalkyl, and the unsaturated aliphatic radicals corresponding to the said saturated hydrocarbon-containing radicals, such as alkenyl, alkynyl, alkenyloxy, alkynyloxy etc. In the case of radicals with carbon atoms, those having 1 to 4 carbon atoms, in particular 1 or 2 carbon atoms, are preferred. As a rule, preferred substituents are from the group consisting of halogen, for example fluorine and chlorine, (C$_1$–C$_4$)alkyl, preferably methyl or ethyl, (C$_1$–C$_4$)haloalkyl, preferably trifluoromethyl, (C$_1$–C$_4$) alkoxy, preferably methoxy or ethoxy, (C$_1$–C$_4$)haloalkoxy, nitro and cyano. Particularly preferred substituents in this connection are methyl, methoxy and chlorine.

Mono- or disubstituted amino is a chemically stable radical from the group of substituted amino radicals which is, for example, N-substituted by one or two identical or different radicals from the group consisting of alkyl, alkoxy, acyl and aryl; preferably monoalkylamino, dialkylamino, acylamino, arylamino, N-alkyl-N-arylamino and N heterocycles; in this connection, alkyl radicals having 1 to 4 carbon atoms are preferred; aryl in this connection is preferably phenyl or substituted phenyl; the definition of acyl in this connection is that indicated hereinafter, preferably (C$_1$–C$_4$) alkanoyl. A corresponding statement applies to substituted hydroxylamino or hydrazino.

Optionally substituted phenyl is preferably phenyl which is unsubstituted or substituted one or more times, preferably up to three times, by identical or different radicals from the group consisting of halogen, $(C_1-C_4)$-alkyl, $(C_1-C_4)$alkoxy, $(C_1-C_4)$haloalkyl, $(C_1-C_4)$haloalkoxy and nitro, for example o-, m- and p-tolyl, dimethylphenyls, 2-, 3- and 4-chlorophenyl, 2-, 3- and 4-trifluoro and -trichlorophenyl, 2,4-, 3,5-, 2,5- and 2,3-dichlorophenyl, o-, m- and p-methoxyphenyl.

An acyl radical is the radical of an organic acid, for example the radical of a carboxylic acid and radicals of acids derived therefrom, such as thiocarboxylic acid, optionally N-substituted iminocarboxylic acids, or the radical of carbonic monoesters, optionally N-substituted carbamic acid, sulfonic acids, sulfinic acids, phosphonic acids, phosphinic acids. Acyl is, for example, formyl, alkylcarbonyl such as $(C_1-C_4$alkyl$)$carbonyl, phenylcarbonyl, where the phenyl ring can be substituted, for example as shown above for phenyl, or alkyloxycarbonyl, phenyloxycarbonyl, benzyloxycarbonyl, alkylsulfonyl, alkylsulfinyl, N-alkyl-1-iminoalkyl and other radicals of organic acids.

The formulae (A), (B1) and (B2) also embrace all the stereoisomers which have the same topological linkage of the atoms, and mixtures thereof. Such compounds contain one or more asymmetric carbon atoms or else double bonds which are not specially indicated in the general formulae. The possible stereoisomers defined by their specific spatial shape, such as enantiomers, diastereomers, Z and E isomers, can be obtained by customary methods from mixtures of stereoisomers or else be prepared by stereoselective reactions in combination with the use of stereochemically pure starting materials.

Compounds of the formula (A) are able to form salts in which the hydrogen of the —$SO_2$—NH— group is replaced by an agriculturally suitable cation. These salts are, for example, metal salts, in particular alkali metal salts or alkaline earth metal salts, especially sodium and potassium salts, or else ammonium salts or salts with organic amines.

Compounds of the formula (B1) are disclosed in EP-A-333 131 (ZA-89/1960), EP-A-269 806 (U.S. Pat. No. 4,891, 057), EP-A-346 620 (AU-A-89/34951), EP-A-174 562, EP-A-346 620 and the International Patent Applications PCT/EP 90/01966 (WO-91/08202) and PCT/EP 90/02020 (WO-91/07874), and German Patent Application P 43 31 448.1 (WO 95/07897 or ZA 94/7120) and literature cited therein or can be prepared by processes described therein or analogous ones. Compounds of the formula (B2) are disclosed in EP-A-86 750, EP-A-94 349 (U.S. Pat. No. 4,902,340), EP-A-191 736 (U.S. Pat. No. 4,881,966) and EP-A-0 492 366 and literature cited therein or can be prepared by the processes described therein or analogous ones. Some compounds are furthermore described in EP-A-0 582 198.

Suitable herbicidal substances according to the invention are those pyrimidine or triazine derivatives of the formula (A) which cannot, or cannot optimally, be used alone in cereals crops and/or corn because they damage the crop plants too much.

Compounds of the formula (A) are disclosed, for example, in WO-A-94/06778, German Patent Applications P 43 35 297.9 (PCT/EP 94/03369, WO 95/10507), P 44 15 049.0 and P 44 19 259.2, and WO-A-94/10154 (U.S. Pat. No. 5,449,812) or can be prepared by processes analogous to those mentioned therein.

Herbicide/safener combinations according to the invention are of particular interest when in the safeners (B1) or (B2)

$R^7$ is hydrogen, $(C_1-C_{18})$alkyl, $(C_3-C_{12})$cycloalkyl, $(C_2-C_8)$alkenyl or $(C_2-C_8)$alkynyl, where the above C-containing radicals are unsubstituted or substituted one or more times, preferably up to three times, by identical or different radicals from the group consisting of halogen, hydroxyl, $(C_1-C_8)$alkoxy, $(C_1-C_8)$alkylmercapto, $(C_2-C_8)$alkenylmercapto, $(C_2-C_8)$alkynylmercapto, $(C_2-C_8)$alkynyloxy, $(C_2-C_8)$alkynyloxy, $(C_3-C_7)$cycloalkyl, $(C_3-C_7)$cycloalkoxy, cyano, mono- and di-$(C_1-C_4$-alkyl$)$amino, carboxyl, $(C_1-C_8)$alkoxycarbonyl, $(C_2-C_8)$alkenyloxycarbonyl, $(C_1-C_8)$alkylmercaptocarbonyl, $(C_2-C_8)$alkynyloxycarbonyl, $(C_1-C_8)$alkylcarbonyl, $(C_2-C_8)$alkenylcarbonyl, $(C_2-C_8)$alkynylcarbonyl, 1-(hydroxyimino)-$(C_1-C_6)$alkyl, 1-[$(C_1-C_4)$alkylimino]-$(C_1-C_4)$alkyl, 1-[$(C_1-C_4)$alkoxyimino]-$C_1-C_6)$alkyl, $(C_1-C_8)$alkylcarbonylamino, $(C_2-C_8)$alkenylcarbonylamino, $(C_2-C_8)$alkynylcarbonylamino, aminocarbonyl, $(C_1-C_8)$alkylaminocarbonyl, di-$(C_1-C_6)$alkylaminocarbonyl, $(C_2-C_6)$alkenylaminocarbonyl, $(C_2-C_6)$alkynylaminocarbonyl, $(C_1-C_8)$alkoxycarbonylamino, $(C_1-C_8)$alkylaminocarbonylamino, $(C_1-C_6)$alkylcarbonyloxy, which is unsubstituted or substituted by halogen, nitro, $(C_1-C_4)$alkoxy or optionally substituted phenyl, or is $(C_2-C_6)$alkenylcarbonyloxy, $(C_2-C_6)$alkynylcarbonyloxy, $(C_1-C_8)$alkylsulfonyl, phenyl, phenyl-$(C_1-C_6)$alkoxy, phenyl-$(C_1-C_6)$alkoxycarbonyl, phenoxy, phenoxy-$(C_1-C_6)$alkoxy, phenoxy-$(C_1-C_6)$alkoxycarbonyl, phenylcarbonyloxy, phenylcarbonylamino, phenyl-$(C_1-C_6)$alkylcarbonylamino, where the 9 last-mentioned radicals are unsubstituted or substituted one or more times, preferably up to three times, in the phenyl ring by identical or different radicals from the group consisting of halogen, $(C_1-C_4)$alkyl, $(C_1-C_4)$alkoxy, $(C_1-C_4)$haloalkyl, $(C_1-C_4)$haloalkoxy and nitro, and radicals of the formulae —SiR'$_3$, —O—SiR'$_3$, R'$_3$Si—$(C_1-C_8)$alkoxy, —CO—O—NR'$_2$, —O—N=CR'$_2$, —N=CR'$_2$, —O—NR'$_2$, —NR'$_2$, CH(OR')$_2$, —O—$(CH_2)_m$—CH(OR')$_2$, —CR'''(OR')$_2$ and —O—$(CH_2)_m$CR'''(OR')$_2$, in which the R' in the said formulae are, independently of one another, hydrogen, $(C_1-C_4)$alkyl, phenyl which is unsubstituted or substituted one or more times, preferably up to three times, by identical or diff rent radicals from the group consisting of halogen, $(C_1-C_4)$alkyl, $(C_1-C_4)$alkoxy, $(C_1-C_4)$haloalkyl, $(C_1-C_4)$haloalkoxy and nitro, or pairwise are a $(C_2-C_6)$alkanediyl chain and m=0 to 6, and R''' is hydrogen or $(C_1-C_4)$alkyl, and a substituted alkoxy radical of the formula R''O—CHR'''CH(OR'')—$(C_1-C_6)$ alkoxy, in which the R'' are, independently of one another, $(C_1-C_4)$alkyl or together are $(C_1-C_6)$alkanediyl and R''' is hydrogen or $(C_1-C_4)$alkyl.

Particularly interesting herbicide/safener combinations according to the invention are also those in which, in the safeners of the formula (B1) or (B2), $R^7$ is hydrogen, $(C_1-C_8)$alkyl or $(C_3-C_7)$cycloalkyl, where the above C-containing radicals are unsubstituted or substituted one or more times by halogen or once or twice, preferably up to once, by radicals from the group consisting of hydroxyl, $(C_1-C_4)$alkoxy, carboxyl, $(C_1-C_4)$alkoxycarbonyl, $(C_2-C_6)$alkenyloxycarbonyl, $(C_2-C_6)$alkynyloxycarbonyl, 1-(hydroxyimino)-$(C_1-C_4)$alkyl, 1-[$(C_1-C_4)$alkylimino]-$(C_1-C_4)$alkyl, 1-[$(C_1-C_4)$alkoxyimino]-$(C_1-C_4)$alkyl and radicals of the formulae —SiR'$_3$, —O—N=CR'$_2$, —N=CR'$_2$, —NR'$_2$ and —O—NR'$_2$, in which the R' in the said formulae are, independently of one another, hydrogen or $(C_1-C_4)$alkyl or pairwise are a $(C_4-C_5)$alkanediyl chain, $R^9$ is hydrogen, $(C_1-C_8)$alkyl, $(C_1-C_6)$haloalkyl, $(C_3-C_7)$cycloalkyl or phenyl, which is unsubstituted or substituted by one or more of the radicals from the group consisting of halogen, cyano, nitro, amino, mono- and di-[$(C_1-C_4)$ alkyl]amino, $(C_1–C_4)$alkyl, $(C_1–C_4)$haloalkyl, $(C_1–C_4)$alkoxy, $(C_1–C_4)$haloalkoxy, $(C_1–C_4)$alkylthio and $(C_1–C_4)$alkylsulfonyl, and $R^{10}$ is hydrogen, $(C_1–C_8)$alkyl, $(C_1–C_8)$haloalkyl, $(C_1–C_4$-alkoxy)-$(C_1–C_4)$alkyl, $(C_1–C_6)$hydroxyalkyl, $(C_3–C_7)$cycloalkyl or tri$(C_1–C_4)$alkylsilyl. and/or X' is hydrogen, halogen, methyl, ethyl, methoxy, ethoxy, $(C_1$ or $C_2)$haloalkyl, preferably hydrogen, halogen or $(C_1$ or $C_2)$haloalkyl.

Safeners preferred in this connection are those in which, in formula (B1),

X' is hydrogen, halogen, nitro or $(C_1–C_4)$haloalkyl, n' is 1, 2 or 3,

Z' is a radical of the formula $OR^7$, $R^7$ is hydrogen, $(C_1–C_8)$alkyl or $(C_3–C_7)$cycloalkyl, where the above C-containing radicals are unsubstituted or substituted one or more times, preferably up to three times, by identical or different halogen radicals or up to twice, preferably up to once, by identical or different radicals from the group consisting of hydroxyl, $(C_1–C_4)$alkoxy, $(C_1–C_4)$alkoxycarbonyl, $(C_2–C_6)$alkenyloxycarbonyl, $(C_2–C_6)$alkynyloxycarbonyl, 1-(hydroxyimino)-$(C_1–C_4)$alkyl, 1-[$(C_1–C_4)$alkylimino]-$(C_1–C_4)$alkyl, 1-[$(C_1–C_4)$alkoxyimino]-$(C_1–C_4)$alkyl and radicals of the formulae —SiR'$_3$, —O—N=R'$_2$, —N=CR'$_2$, —NR'$_2$ and —O—NR'$_2$, where the radicals R' in the said formulae are, independently of one another, hydrogen or $(C_1–C_4)$alkyl or pairwise are $(C_4$ or $C_5)$alkanediyl, $R^9$ is hydrogen, $(C_1–C_8)$alkyl, $(C_1–C_6)$haloalkyl, $(C_3–C_7)$cycloalkyl or phenyl, which is unsubstituted or substituted by one or more radicals from the group consisting of halogen, $(C_1–C_4)$alkyl, $(C_1–C_4)$alkoxy, nitro, $(C_1–C_4)$haloalkyl and $(C_1–C_4)$haloalkoxy, and $R^{10}$ is hydrogen, $(C_1–C_8)$alkyl, $(C_1–C_8)$haloalkyl, $(C_1–C_4)$alkoxy)-$(C_1–C_4)$alkyl, $(C_1–C_6)$hydroxyalkyl, $(C_3–C_7)$cycloalkyl or tri$(C_1–C_4)$alkylsilyl.

Preferred safeners in this connection are also those in which, in formula (B2),

X' is hydrogen, halogen or $(C_1–C_4)$haloalkyl, n' is 1, 2 or 3, where $(X')_{n'}$ is preferably 5-Cl, Z' is a radical of the formula $OR^7$, R* is $CH_2$, and $R^7$ is hydrogen, $(C_1–C_8)$alkyl, $(C_1–C_8)$haloalkyl or $(C_1–C_4)$alkoxy-$(C_1–C_4)$alkyl, preferably $(C_1–C_8)$alkyl.

Particularly preferred safeners in this connection are those in which, in formula (B1), W' is (W1), X' is hydrogen, halogen or $(C_1–C_2)$haloalkyl, n' is 1, 2 or 3, where $(X')_{n'}$ is preferably 2,4-Cl$_2$, Z' is a radical of the formula $OR^7$, $R^7$ is hydrogen, $(C_1–C_8)$alkyl, $(C_1–C_4)$haloalkyl, $(C_1–C_4)$hydroxyalkyl, $(C_3–C_7)$cycloalkyl, $(C_1–C_4)$alkoxy-$(C_1–C_4)$alkyl, tri-$(C_1–C_2)$alkylsilyl, preferably $(C_1–C_4)$alkyl, $R^9$ is hydrogen, $(C_1–C_8)$alkyl, $(C_1–C_4)$haloalkyl or $(C_3–C_7)$cycloalkyl, preferably hydrogen or $(C_1–C_4)$alkyl, and $R^{10}$ is hydrogen, $(C_1–C_8)$alkyl, $(C_1–C_4)$haloalkyl, $(C_1–C_4)$hydroxyalkyl, $(C_3–C_7)$cycloalkyl, $(C_1–C_4)$alkoxy-$(C_1–C_4)$alkyl or tri-$(C_1–C_2)$alkylsilyl, preferably hydrogen or $(C_1–C_4)$alkyl.

Also particularly preferred are herbicidal compositions in which, in formula (B1)

W' is (W2),

X' is hydrogen, halogen or $(C_1–C_2)$haloalkyl, n' is 1, 2 or 3, where $(X')_{n'}$ is preferably 2,4-Cl$_2$, Z' is a radical of the formula $OR^7$, $R^7$ is hydrogen, $(C_1–C_8)$alkyl, $(C_1–C_4)$haloalkyl, $(C_1–C_4)$hydroxyalkyl, $(C_3–C_7)$cycloalkyl, $(C_1–C_4$-alkoxy)-$C_1–C_4$-alkyl, tri-$(C_1–C_2)$alkylsilyl, preferably $(C_1–C_4)$alkyl, and $R^9$ is hydrogen, $(C_1–C_8)$alkyl, $(C_1–C_4)$haloalkyl, $(C_3–C_7)$cycloalkyl or phenyl, preferably hydrogen or $(C_1–C_4)$alkyl.

Also particularly preferred in this connection are safeners in which, in formula (B1), W' is (W3), X' is hydrogen, halogen or $(C_1–C_2)$haloalkyl, n' is 1, 2 or 3, where $(X')_{n'}$ is preferably 2-4-Cl$_2$, Z' is a radical of the formula $OR^7$, $R^7$ is hydrogen, $(C_1–C_8)$alkyl, $(C_1–C_4)$haloalkyl, $(C_1–C_4)$hydroxyalkyl, $(C_3–C_7)$cycloalkyl, $(C_1–C_4)$alkoxy-$(C_1–C_4)$alkyl, tri-$(C_1–C_2)$alkylsilyl, preferably $(C_1–C_4)$alkyl, and $R^9$ is $(C_1–C_8)$alkyl or $(C_1–C_4)$haloalkyl, preferably $C_1$-haloalkyl.

Also particularly preferred in this connection are safeners in which, in formula (B1), W' is (W4), X' is hydrogen, halogen, nitro, $(C_1–C_4)$alkyl or $(C_1–C_2)$haloalkyl, preferably $CF_3$, or $(C_1–C_4)$alkoxy, n' is 1, 2 or 3, m' is 0 or 1, Z' is a radical of the formula $OR^7$, and $R^7$ is hydrogen, $(C_1–C_4)$alkyl, carboxy-$(C_1–C_4)$alkyl or $(C_1–C_4)$alkoxycarbonyl-$(C_1–C_4)$alkyl, preferably $(C_1–C_4)$alkoxy-CO—CH$_2$—, $(C_1–C_4)$alkoxy-CO—C(CH$_3$)H—, HO—CO—CH$_2$— or HO—CO—C(CH$_3$)H— and $R^9$ is H, $(C_1–C_4)$alkyl, $(C_1–C_4)$haloalkyl, $(C_3–C_7)$cycloalkyl or phenyl which is unsubstituted or substituted by one or more radicals from the group consisting of halogen, $(C_1–C_4)$alkyl, $(C_1–C_4)$haloalkyl, nitro, cyano and $(C_1–C_4)$alkoxy.

The following groups of compounds are suitable examples of safeners for the abovementioned herbicidal active substances (A):

a) compounds of the dichlorophenylpyrazoline-3-carboxylic acid type (i.e. of the formula (B1) in which W'=W1 and $(X')_{n'}$=2,4-Cl$_2$), preferably compounds such as ethyl 1-(2,4-dichlorophenyl)-5-(ethoxycarbonyl)-5-methyl-2-pyrazoline-3-carboxylate (B1-1) and related compounds as described in WO 91/07874, b) derivatives of dichlorophenylpyrazolecarboxylic acid (i.e. of the formula (B1) in which W'=W2 and $(X')_{n'}$=2,4-Cl$_2$), preferably compounds such as ethyl 1-(2,4-dichlorophenyl)-5-methylpyrazole-3-carboxylate (B1-2), ethyl 1-(2,4-dichlorophenyl)-5-isopropylpyrazole-3-carboxylate (B1-3), thyl 1-(2,4-dichlorophenyl)-5-(1,1-dimethylethyl)pyrazole-3-carboxylate (B1-4), ethyl 1-(2,4-dichlorophenyl)-5-phenylpyrazole-3-carboxylate (B1-5) and related compounds as described in EP-A-333 131 and EP-A-269 806.

c) Compounds of the triazolecarboxylic acid type (i.e. of the formula (B1), in which W'=W3 and $(X')_{n'}$=2,4-Cl$_2$), preferably compounds such as fenchlorazole, i.e. ethyl 1-(2,4-dichlorophenyl)-5-trichloromethyl-(1H)-1,2,4-triazole-3-carboxylate (B1-6) and related compounds (see EP-A-174 562 and EP-A-346 620);

d) Compounds of the type of 5-benzyl- or 5-phenyl-2-isoxazoline-3-carboxylic acid or of 5,5-diphenyl-2-isoxazoline-3-carboxylic acid, preferably compounds such as ethyl 5-(2,4-dichlorobenzyl)-2-isoxazoline-3-carboxylate (B1-7) or ethyl 5-phenyl-2-isoxazoline-3-carboxylate (B1-8) and related compounds as described in WO 91/08202, and ethyl (B1-9) or n-propyl (B1-10) 5,5-diphenyl-2-isoxazolinecarboxylate or ethyl 5-(4-fluorophenyl)-5-phenyl-2-isoxazoline-3-carboxylate (B1-11), as described in German Patent Application P 43 31 448.1 (WO-A-95/07897).

e) Compounds of the 8-quinolinoxyacetic acid type, for example those of the formula (B2) in which $(X')_n=5$-Cl, hydrogen, $Z'=OR^7$, $R^*=CH_2$, preferably compounds such as 1-methylhexyl (5-chloro-8-quinolinoxy)acetate (B2-1), 1,3-dimethylbutyl (5-chloro-8-quinolinoxy)acetate (B2-2), 4-allyloxybutyl (5-chloro-8-quinolinoxy)acetate (B2-3), 1-allyloxy-2-propyl (5-chloro-8-quinolinoxy)acetate (B2-4), ethyl (5-chloro-8-quinolinoxy)acetate (B2-5), methyl (5-chloro-8-quinolinoxy)acetate (B2-6), allyl (5-chloro-8-quinolinoxy)acetate (B2-7), 2-(2-propylideneiminoxy)ethyl (5-chloro-8-quinolinoxy)acetate (B2-8), 2-oxopropyl (5-chloro-8-quinolinoxy)acetate (B2-9) and related compounds as described in EP-A-86 750, EP-A-94 349 and EP-A-191 736 or EP-A-0 492 366.

f) Compounds of the (5-chloro-8-quinolinoxy)malonic acid type (i.e. of the formula (B2) in which $(X')_n=5$-Cl, $Z'=OR^7$, $R^*=$—CH(COO-alkyl)), preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds as described in EP-A-0 582 198.

g) Active substances of the type of phenoxyacetic or -propionic acid derivatives or of aromatic carboxylic acids such as, for example, 2,4-dichlorophenoxyacetic acid (ester) (2,4-D), 4-chloro-2-methylphenoxypropionic ester (mecoprop), MCPA or 3,6-dichloro-2-methoxybenzoic acid (ester) (dicamba).

Particularly interesting herbicides/safener combinations according to the invention are those in which, in compounds of the formula (A) or their salts, $R^1$ is an aliphatic hydrocarbon radical which has up to 24 carbon atoms and which is unsubstituted or substituted, preferably $(C_1-C_6)$alkyl, $(C_2-C_6)$alkenyl, $(C_2-C_6)$alkynyl, $(C_3-C_6)$cycloalkyl, each of the four last-mentioned radicals being unsubstituted or substituted by one or more radicals from the group consisting of halogen, CN, $(C_1-C_4)$alkoxy, $(C_1-C_4)$alkylthio, $(C_1-C_4)$ haloalkoxy, mono-$(C_1-C_4$alkyl)amino, di-$(C_1-C_4$alkyl)amino, $(C_1-C_4)$alkylsulfonyl, $(C_1-C_4$-alkyl)aminocarbonyl, di$(C_1-C_4$alkyl)aminocarbonyl, phenyl and substituted phenyl, or a radical of the type heterocyclyl or heterocyclyl-$(C_1-C_4)$alkyl having 3 to 7 ring atoms, preferably a radical of formulae A-1 to A-13

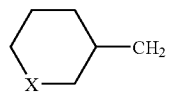
A-1

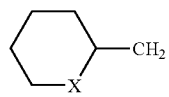
A-2

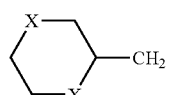
A-3

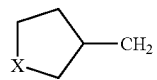
A-4

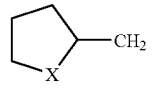
A-5

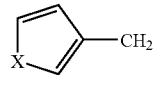
A-6

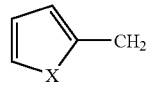
A-7

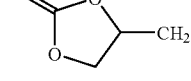
A-8

A-9

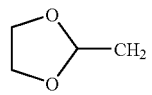
A-10

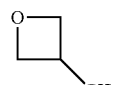
A-11

A-12

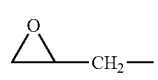
A-13

X is O, S, S(O) or $SO_2$, preferable O, $R^2$ is H, OH, an aliphatic hydrocarbon radical or hydrocarbon-oxy radical which is unsubstituted or substituted and contains a total of up to 18, preferably up to 12, in particular up to 8, carbon atoms, preferably H, OH, $(C_1-C_6)$alkyl, $(C_3-C_7)$cycloalkyl, $(C_2-C_6)$alkenyl, $(C_2-C_6)$alkynyl, $(C_1-C_6)$alkoxy, $(C_3-C_7)$cycloalkoxy, $(C_2-C_6)$alkenyloxy, $(C_2-C_6)$alkynyloxy, the eight last-mentioned radicals being unsubstituted or substituted by one or more radicals from the group consisting of $(C_1-C_4)$alkoxy, $(C_1-C_4)$haloalkoxy, $(C_2-C_4)$alkenyloxy, $(C_2-C_4)$haloalkenyloxy, $(C_2-C_4)$alkynyloxy, $(C_2-C_4)$haloalkynyloxy, $(C_1-C_4)$alkylthio, $(C_1-C_4)$haloalkylthio, halogen, OH, $NH_2$, mono- and di[$(C_1-C_4)$alkyl]amino, CN, $NO_2$, $CONH_2$, CHO, [$(C_1-C_6)$alkyl]carbonyl, $(C_1-C_4)$alkylsulfonyl, [$(C_1-C_4)$alkoxy]carbonyl, mono- and di-[$(C_1-C_4)$alkyl]-aminocarbonyl, and in the case of cyclic radicals also $(C_1-C_4)$alkyl and $(C_1-C_4)$haloalkyl, $R^3$ is CO—$R^{11}$, CO—$OR^{12}$, CO—$NR^{13}R^{14}$, CO—$SR^{15}$, CS—$R^{16}$, CS—$OR^{17}$, CS—$NR^{18}R^{19}$, CS—$SR^{20}$, $SO_2R^{21}$, $SO_2NR^{22}R^{23}$, $R^{11}$ is H, $(C_1-C_6)$alkyl, $(C_2-C_6)$alkenyl, $(C_2-C_6)$alkynyl, the three last-mentioned radicals being, independently of one another, unsubstituted or substituted by one or more radicals from the group consisting of halogen, $(C_1-C_4)$alkoxy, $(C_1-C_4)$alkylthio and $NR^{24}R^{25}$, or unsubstituted or substituted $(C_3-C_8)$cycloalkyl, unsubstituted or substituted phenyl, unsubstituted or substituted heteroaryl or phenyl-$(C_1-C_4)$alkyl which is unsubstituted or substituted on the phenyl ring, $R^{12}$ is $(C_1-C_6)$alkyl, $(C_2-C_6)$alkenyl, $(C_2-C_6)$alkynyl, the three last-mentioned radicals being, independently of one another, unsubstituted or substituted by one or more radicals from the group consisting of halogen, $(C_1-C_4)$alkoxy, $(C_1-C_4)$alkylthio and $NR^{26}R^{27}$, or, $(C_3-C_6)$cycloalkyl which is unsubstituted or substituted by one or more radicals from the group consisting of halogen, $(C_1-C_4)$alkyl and $(C_1-C_4)$alkoxy, or $(C_3-C_6)$cycloalkyl-$(C_1-C_3)$alkyl, $R^{13}$ is H, $(C_1-C_6)$alkyl, $(C_2-C_6)$alkenyl, $(C_2-C_6)$alkynyl, the three last-mentioned radicals being, independently of one another, unsubstituted or substituted by one or more radicals from the halogen group, or is $[(C_1-C_6)$alkoxy$]$carbonyl, $(C_1-C_4)$alkoxy or OH, $R^{14}$ is H, $(C_1-C_6)$alkyl, $(C_2-C_6)$alkenyl, $(C_2-C_6)$alkynyl, the three last-mentioned radicals being, independently of one another, unsubstituted or substituted by one or more radicals from the group consisting of halogen, $(C_1-C_4)$alkoxy, $(C_1-C_4)$alkylthio and $NR^{28}R^{29}$ or $NR^{13}R^{14}$ is a heterocyclic radical which, besides the nitrogen atom, can contain further hetero units from the group consisting of O, N, S, SO or $SO_2$ in the ring framework and which is unsubstituted or substituted by one or more radicals from the group consisting of halogen, OH, $NH_2$, $NHCH_3$, $N(CH_3)_2$, CN, $CONHCH_3$, $CO_2CH_3$, $COCH_3$, $CON(CH_3)_2$, CHO, $(C_1-C_3)$alkyl, $CONH_2$, $(C_1-C_3)$alkoxy, $(C_1-C_3)$haloalkoxy, $(C_1-C_3)$haloalkyl and the oxo group, $R^{15}$ is a radical analogous to $R^{12}$,
$R^{16}$ is a radical analogous to $R^{11}$,
$R^{17}$ is a radical analogous to $R^{12}$,
$R^{18}$ is a radical analogous to $R^{13}$,
$R^{19}$ is a radical analogous to $R^{14}$,
or $NR^{18}R^{19}$ is a radical analogous to $NR^{13}R^{14}$,
$R^{20}$ is a radical analogous to $R^{12}$,
$R^{21}$ is $(C_1-C_6)$alkyl, $(C_2-C_6)$alkenyl, $(C_2-C_6)$alkynyl, the three last-mentioned radicals being, independently of one another, unsubstituted or substituted by one or more radicals from the group consisting of halogen, $(C_1-C_4)$alkoxy, $(C_1-C_4)$alkylthio and $NR^{30}R^{31}$,
$R^{22}$ is a radical analogous to $R^{13}$,
$R^{23}$ is a radical analogous to $R^{14}$ or
$NR^{22}R^{23}$ is a radical analogous to $NR^{13}R^{14}$,
$R^{24}$ is H, $(C_1-C_4)$alkyl, $(C_1-C_4)$haloalkyl, $(C_1-C_4)$alkenyl, $(C_1-C_4)$haloalkenyl, $(C_1-C_4)$alkoxys $(C_1-C_4)$haloalkoxy or hydroxyl,
$R^{25}$ is H, $(C_1-C_4)$alkyl, $(C_1-C_4)$haloalkyl, $(C_1-C_4)$alkenyl or $(C_1-C_4)$haloalkenyl,
$R^{26}$ is analogous to $R^{24}$,
$R^{27}$ is analogous to $R^{25}$,
$R^{28}$ is analogous to $R^{24}$,
$R^{29}$ is analogous to $R^{25}$,
$R^{30}$ is analogous to $R^{24}$ and
$R^{31}$ is analogous to $R^{25}$.

The term "analogous" in a definition such as "$R^{15}$ is a radical analogous to $R^{12}$" means that $R^{15}$ and $R^{12}$ are identical or different radicals as listed in the definition of $R^{12}$.

Also of particular interest are herbicide/safener combinations according to the invention where, in the compounds of the formula (A) and salts thereof, $R^1$ is $(C_1-C_6)$alkyl, $(C_2-C_6)$alkenyl, $(C_2-C_6)$alkynyl, $(C_3-C_6)$cycloalkyl, each of the four last-mentioned radicals being unsubstituted or substituted by one or more radicals from the group consisting of F, Cl, Br, I, CN, $OCH_3$, $OCF_3$, $N(CH_3)_2$, $SO_2CH_3$, $CO_2CH_3$, $CO_2N(CH_3)_2$ and phenyl, or a group of said formula A-1 to A-13,
$R^2$ is H, $(C_1-C_4)$alkyl, $(C_2-C_4)$alkenyl, $(C_2-C_4)$alkynyl, $(C_3-C_6)$cycloalkyl or $(C_1-C_4)$haloalkyl,
$R^3$ is CO—$R^{11}$, CO—$OR^{12}$, CO—$NR^{13}R^{14}$ or $SO_2R^{21}$,
$R^4$ is halogen, $(C_1-C_3)$alkyl or $(C_1-C_3)$alkoxy,
n is 0 or 1,
m is 0 or 1,
$R^5$ is H or $CH_3$,
$R^{11}$ is H, $(C_1-C_6)$alkyl, $(C_2-C_4)$alkenyl, $(C_2-C_4)$alkynyl, $(C_1-C_4)$haloalkyl, $(C_1-C_4)$alkoxy-$(C_1-C_4)$alkyl, phenyl or heteroaryl with 5 or 6 ring atoms, each of the two last-mentioned radicals being unsubstituted or substituted,
$R^{12}$ is a radical analogous to $R^{11}$, apart from hydrogen,
$R^{13}$, $R^{14}$ are, independently of one another, H or $(C_1-C_4)$alkyl,
$R^{21}$ is $(C_1-C_4)$alkyl, $(C_1-C_4)$haloalkyl or $(C_1-C_4)$alkoxy-$(C_1-C_4)$alkyl,
one of the radicals $X^1$ and $X^2$ is halogen, $(C_1-C_2)$alkyl, $(C_1-C_2)$alkoxy, $(C_1-C_2)$alkylthio, each of the three last-mentioned radicals being unsubstituted or substituted by one or more radicals from the group consisting of halogen, $(C_1-C_2)$alkoxy and $(C_1-C_2)$alkylthio, or mono- or di$(C_1-C_2$-alkyl)amino, preferably halogen, methyl or methoxy, and
the other one of the radicals $X^1$ and $X^2$ is $(C_1-C_2)$alkyl, $(C_1-C_2)$haloalkyl, $(C_1-C_2)$alkoxy, $(C_1-C_2)$haloalkoxy or $(C_1-C_2)$alkylthio, preferably methyl or methoxy,
Z is CH or N.

Preferred compounds of the formula (I) and salts thereof according to the invention are those in which
$R^1$ is $(C_1-C_4)$alkyl, preferably methyl or ethyl,
$R^2$ is H, $(C_1-C_4)$alkyl, preferably methyl or ethyl,
$R^3$ is formyl, acetyl, n-propionyl, i-propionyl, 2-methylpropionyl, n-butanoyl, cyclopropylcarbonyl, methoxycarbonyl, ethoxycarbonyl, trifluoroacetyl, methylsulfonyl,
m is 0 or 1,
n is zero,
$R^5$ is hydrogen,
A is $CH_2$,
Q is an oxygen atom or $N(CH_3)$,
$X^1$ is $OCH_3$, $OC_2H_5$ or Cl,
$X^2$ is $OCH_3$ or $OC_2H_5$,
Z is CH or N.

The safeners (antidotes) of the formulae (B1) and (B2), for example safeners of the abovementioned groups a) to g), reduce or suppress phytotoxic effects which may occur on use of the herbicidal active substances of the formula (A) in crops of useful plants, with negligible impairment of the activity of these herbicidal active substances on harmful plants. This makes it possible very considerably to extend the range of uses of conventional crop protection agents and extend it, for example, to crops such as wheat, barley, corn and other graminaceous crops in which use of the herbicides has hitherto been impossible or possible to only a limited extent, that is to say in low doses with not a very broad action.

The herbicidal active substances and the safeners mentioned can be applied together (as ready-to-use formulation or in the tankmix process) or in any desired sequence one after the other. The safener:herbicidal active substance ratio by weight can vary within wide limits and is preferably in the range from 1:100 to 100:1, in particular from 1:10 to 10:1. The optimal quantities of herbicidal active substance and safener in each case depend on the type of herbicidal active substance used or on the safener used and on the type of crop to be treated and can be determined by appropriate preliminary tests in each case.

The main areas of use of the safeners are, in particular, corn and cereals crops (wheat, rye, barley, oats), rice, sorghum, but also cotton and soybean, preferably cereals and corn.

The safeners of the formulae (B1) and (B2) can, depending on their properties, be used for pretreatment of the seed of the crop plant (seed dressing) or be introduced before sowing into the seed furrows or applied together with the herbicide before or after emergence of the plants. Pre-emergence treatment includes both treatment of the growing area before sowing and treatment of the growing areas which have been sown but as yet show no growth. Use together with the herbicide is preferred. Tank mixes or ready-to-use formulations can be used for this purpose.

The safener application rates required may vary within wide limits depending on the indication and herbicidal active substance used and are, as a rule, in the range from 0.001 to 5 kg, preferably 0.005 to 0.5 kg, of active substance per hectare.

The present invention therefore also relates to a method for protecting plants from the phytotoxic side effects of herbicides of the formula (A), which comprises applying an effective quantity of a compound of the formula (B1) and/or (B2) before, after or at the same time as the herbicidal active substance of the formula (A) to the plants, plant seeds or the growing area.

The compounds of the formulae (B1) and (B2) and combinations thereof with one or more of said herbicidal active substances can be formulated in a variety of ways, depending on the specified biological and/or physico-chemical parameters. Examples of possible and suitable formulations are: wettable powders (WP), emulsifiable concentrates (EC), water-soluble powders (SP), water-soluble concentrates (SL), concentrated emulsions (BW) such as oil-in-water and water-in-oil emulsions, sprayable solutions or emulsions, capsule suspensions (CS), oil- or water-based dispersions (SC), suspoemulsions, suspension concentrates, dustable powders (DP), oil-miscible solutions (OL), seed dressings, granules (GR) in the form of micro-, sprayable, absorption and adsorption granules, granules for soil application or distribution, water-soluble granules (SG), water-dispersible granules (WG), ULV formulations, microcapsules and waxes.

These individual formulation types are known in principle and are described, for example, in: Winnacker-Küchler, "Chemische Technologie" [Chemical Technology], Volume 7, C. Hauser Verlag, Munich, 4th Edition, 1986; Wade van Valkenburg, "Pesticide Formulations", Marcel Dekker N.Y., 1973; K. Martens, "Spray Drying Handbook", 3rd Ed. 1979, G. Goodwin Ltd. London.

The formulation auxiliaries required, such as inert materials, surfactants, solvents and other additives are likewise known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äithylenoxidaddukte" [Surface-active Ethylene Oxide Adducts], Wiss. Verlagsgesell., Stuttgart 1976; Winnacker-Küchler, "Chemische Technologie" [Chemical Technology], Volume 7, C. Hauser Verlag, Munich, 4th Edition, 1986.

It is also possible on the basis of these formulations to produce combinations with other substances with pesticidal activity, such as, for example, insecticides, acaricides, herbicides, fungicides, and with safeners, fertilizers and/or growth regulators, for example in the form of a ready-to-use formulation or tankmix.

Wettable powders are products which can be uniformly dispersed in water and which, besides the active substance and apart from a diluent or inert substance, also contain ionic and/or nonionic surfactants (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium ligninsulfonate, sodium 2,2'-dinaphthylmethane-6,6'-disulfonate, sodium dibutylnaphthalenesulfonate or else oleoylmethyltaurine sodium salt. The wettable powders are produced by finely milling the herbicidal active substances, for example in customary apparatus such as hammer mills, integral fan mills and air jet mills and mixed, simultaneously or subsequently, with the formulation auxiliaries.

Emulsifiable concentrates are produced by dissolving the active substance in an organic solvent, for example butanol, cyclohexanone, dimethylformamide, xylene or else higher-boiling aromatic compounds or hydrocarbons or mixtures of the organic solvents with the addition of one or more ionic and/or nonionic surfactants (emulsifiers). Examples of emulsifiers which can be used are: calcium alkylarylsulfonates such as Ca dodecylbenzenesulfonate or nonionic emulsifiers such as fatty acid polyglycol ethers, alkylaryl polyglycol ethers, fatty alcohol polyglycol ethers, propylene oxide/ethylene oxide condensation products, alkyl polyethers, sorbitan esters such as, for example, sorbitan fatty acid esters or polyoxyethylene sorbitan esters such as, for example polyoxyethylene sorbitan fatty acid esters.

Dustable powders are obtained by milling the active substance with finely divided solid substances, for example talc, natural clays such as kaolin, bentonit and pyrophyllite, or diatomaceous earth.

Suspension concentrates can be water- or oil-based. They can be produced, for example, by wet milling using commercially available bead mills and, where appropriate, adding surfactants as have already been listed above, for example, for the other types of formulation.

Emulsions, for example oil-in-water emulsions (EW), can be produced, for example, by means of stirrers, colloid mills and/or static mixers using aqueous organic solvents and, where appropriate, surfactants as have already been listed above, for example, for the other types of formulation.

Granules can be produced either by spraying the active substance onto granulated inert adsorbent material or by applying active substance concentrates by means of adhesives, for example polyvinyl alcohol, sodium polyacrylate or else mineral oils, onto the surface of carriers such as sand, kaolinites or granulated inert material. It is also possible for suitable active substances to be granulated in the way customary for producing fertilizer granules—if required mixed with fertilizers.

Water-dispersible granules are, as a rule, produced by customary processes such as spray drying, fluidized bed granulation, plate granulation, mixing with high-speed mixers and extrusion without solid inert material.

On the production of plate, fluidized bed, extruder and spray granules, see, for example, processes in "Spray-Drying Handbook" 3rd Ed., 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, pages 8–57.

For further details of the formulation of crop protection agents, see, for example, G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

The agrochemical compositions contain, as a rule, from 0.1 to 99% by weight, in particular 0.1 to 95% by weight, of active substances of the formula (B1) and/or (B2) or of the herbicide/antidote active substance mixture (A) and (B1) and/or (B2) and 1 to 99.9% by weight, in particular 5 to 99.8% by weight, of a solid or liquid additive and 0 to 25% by weight, in particular 0.1 to 25% by weight, of a surfactant.

The active substance concentration in wettable powders is, for example, about 10 to 90% by weight, and the remainder up to 100% by weight consists of customary formulation ingredients. The active substance concentration in emulsifiable concentrates is about 1 to 80% by weight. Formulations in dust form contain about 1 to 20% by weight of active substances, and sprayable solutions contain about 0.2 to 20% by weight of active substances. In granules, such as water-dispersible granules, the active substance content partly depends on whether the active compound is in liquid or solid form. As a rule, the content in water-dispersible granules is between 10 and 90% by weight.

The said active substance formulations additionally contain where appropriate the adhesives, wetting agents, dispersants, emulsifiers, penetration promoters, preservatives, frost protection agents and solvents, fillers, carriers and dyes, antifoam agents, evaporation inhibitors and agents influencing the pH and viscosity which are customary in each case.

Examples of active substances which can be used as combination partners for the active substances according to the invention in mix formulations or in a tankmix are those described, for example in Weed Research 26, 441–445 (1986), or "The Pesticide Manual", 9th edition, The British Crop Protection Council, 1990/91, Bracknell, England, and literature cited therein. The following active substances may be mentioned as examples of herbicides which are disclosed in the literature and can be combined with the compounds of the formula (I). (Note: the compounds are identified either by the "common name" according to the International Organization for Standardization (ISO) or by the chemical name, where appropriate together with a conventional code number): acetochlor; acifluorfen; aclonifen; AKH 7088, i.e. [[[1-[5-[2-chloro-4-(trifluoromethyl)phenoxy]-2-nitrophenyl]-2-methoxyethylidene]amino]oxy]acetic acid and -acetic acid methyl ester; alachlor; alloxydim; ametryn; amidsulfuron; amitrol; AMS, i.e. ammonium sulfamate; anilofos; asulam; atrazin; azimsulfurone (DPX-A8947); aziprotryn; barban; BAS 516 H, i.e. 5-fluoro-2-phenyl-4H-3,1-benzoxazin-4-one; benazolin; benfluralin; benfuresate; bensulfuron-methyl; bensulide; bentazone; benzofenap; benzofluor; benzoylpropethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; caferstrole (CH-900):; carbetamide; carentrazone (ICI-A0051); CDAA, i.e. 2-chloro-N,N-di-2-propenylacetamide; CDEC, i.e. 2-chloroallyl diethyldithiocarbamate; chlomethoxyfen; chloramben; chlorazifop-butyl, chlormesulon (ICI-A0051); chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomazone; clomeprop; cloproxydim; clopyralid; cumyluron, (JC 940); cyanazine; cycloate; cyclosulfamuron (AC 104); cycloxydim; cycluron; cyhalofop and its ester derivatives (for example butyl ster, DEH-112); cyperquat; cyprazine; cyprazole; daimuron; 2,4-DB; dalapon; desmedipham; desmetryn; di-allate; dicamba; dichlobenil; dichlorprop; diclofop and its esters such as diclofop-methyl; diethatyl; difenoxuron; difenzoquat; diflufenican; dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazineethyl; EL 177, i.e. 5-cyano-1-(1,1-dimethylethyl)-N-methyl-1H-pyrazole-4-carboxamide; endothal; EPTC; esprocarb; ethafluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl]ethanesulfonamide; ethoxyfen and its esters (for example ethyl ester, HN-252); etobenzanid (HW 52); fenoprop; fenoxan, fenoxaprop and fenoxaprop-P and their esters, for example fenoxaprop-P ethyl and fenoxaprop-ethyl; fenoxydim; fenuron; flamprop-methyl; flazasulfuron; fluazifop and fluazifop-P and their esters, for example fluazifop-butyl and fluazifop-P-butyl; fluchloralin; flumetsulam; flumeturon; flumiclorac and its esters (for example pentyl ester, S-23031); flumioxazin (S-482); flumipropyn; flupoxam (KNW-739); fluorodifen; fluoroglycofen-ethyl; flupropacil (UBIC-4243); fluridone; flurochloridone; fluroxypyr; flurtamone; fomesafen; fosamine; furyloxyfen; glufosinate; glyphosate; halosaten; halosulfuron and its esters (for example methyl ester, NC-319); haloxyfop and its esters; haloxyfop-P (=R-haloxyfop) and its esters; hexazinone; imazamethabenz-methyl; imazapyr; imazaquin and salts such as the ammonium salt; imazethamethapyr; imazethapyr; imazosulfuron; ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metham; methazole; methoxyphenone; methyldymron; metabenzuron, methobenzuron; metobromuron; metolachlor; metosulam (XRD 511); metoxuron; metribuzin; metsulfuron-methyl; MH; molinat ; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; naproanilide; naptalam; NC 310, i.e. 4-(2,4-dichlorobenzoyl)-1-methyl-5-benzyloxypyrazole; neburon; nicosulfuron; nipyrachlophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031);

pyroxofop and its esters (for example propargyl ester); quinclorac; quinmerac; quinofop and its ester derivatives, quizalofop and quizalofop-P and their ester derivatives, for example quizalofop-ethyl; quizalofop-P-tefuryl and -ethyl; renriduron; rimsulfuron (DPX-E9636); S 275, i.e. 2-[4-chloro-2-fluoro-5-(2-propynyloxy)phenyl]-4,5,6,7-tetrahydro-2H-indazole; seebumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; sulfentrazon (FMC-97285, F-6285); sulfazuron; sulfometuron-methyl; sulfosat (ICI-A0224); TCA; tebutam (GCP-5544); tebuthiuron; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluron; thizopyr (Mon-13200); thidiazimin (SN-124085); thifensulfuronmethyl; thiobencarb; tiocarbazil; tralkoxydim; triallate, triasulfuron; triazofenamide; tribenuron-methyl; triclopyr; tridiphane; trietazine; trifluralin; triflusulfuron and esters (for exampl methyl ester, DPX-66037); trimeturon; tsitodef; vernolate; WL 110547, i.e. 5-phenoxy-1-[3-(trifluoromethyl)phenyl]-1H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

For application, the formulations which are in the customary commercial form are, where appropriate, diluted in a usual way, for example in the case of wettable powders, emulsifiable concentrates, dispersions and water-dispersible granules using water. Compositions in dust form, soil and distribution granules, and sprayable solutions, are not normally diluted with further inert substances before application.

The required application rate of the compounds of the formula (A) according to the invention varies with the external conditions such as temperature, humidity, the nature of the herbicide used, etc. It can be varied within wide limits, for example between 0.001 and 10.0 kg/ha or more active substance, but is preferably between 0.005 and 5 kg/ha.

The following examples serve to illustrate the invention:

A. FORMULATION EXAMPLES a) A dust composition is obtained by mixing 10 parts by weight of a compound of the formula (B1) and/or (B2) or of an active substance mixture consisting of a herbicidal active substance of the formula (A) and of a safener of the formula (B1) and/or (B2) and 90 parts by weight of talc as inert substance and comminuting in a crusher mill.

b) A wettable powder which can easily be dispersed in water is obtained by mixing 25 parts by weight of a compound of the formula (B1) and/or (B2) or of an active substance mixture consisting of a herbicidal active substance of the formula (A) and of a safener of the formula (B1) and/or (B2), 64 parts by weight of kaolin-containing quartz as inert substance, 10 parts by weight of potassium ligninsulfonate and 1 part by weight of oleoylmethyltaurine sodium salt as wetting agent and dispersant and milling in a pinned disk mill.

c) A dispersion concentrate which can easily be dispersed in water is obtained by mixing 20 parts by weight of a compound of the formula (B1) and/or (B2) or of an active substance mixture consisting of a herbicidal active substance of the formula (A) and of a safener of the formula (B1) and/or (B2), 6 parts by weight of alkylphenol polyglycol ether (®Triton X 207), 3 parts by weight of isotridecanol polyglycol ether (8 EO) and 71 parts by weight of paraffinic mineral oil (boiling range, for example, about 255 to above 277° C.) and milling in a ball mill to a fineness below 5 microns.

d) An emulsifiable concentrate is obtained from 15 parts by weight of a compound of the formula (B1) and/or (B2) or of an active substance mixture consisting of a herbicidal active substance of the formula (A) and of a safener of the formula (B1) and/or (B2), 75 parts by weight of cyclohexanone as solvent and 10 parts by weight of ethoxylated nonylphenol as emulsifier.

| e) Water-dispersible granules are obtained by mixing | |
|---|---|
| 75 parts by weight | of a compound of the formula (B1) and/or (B2) or of an active substance mixture consisting of a herbicidal active substance of the formula (A) and of a safener of the formula (B1) and/or (B2), |
| 10 parts by weight | calcium ligninsulfonate, |
| 5 parts by weight | sodium lauryl sulfate, |
| 3 parts by weight | polyvinyl alcohol and |
| 7 parts by weight | kaolin | milling in a pinned disk mill and granulating the powder in a fluidized bed by spraying on water as granulation liquid.

| f) Water-dispersible granules are also obtained by homogenizing and precomminuting | |
|---|---|
| 25 parts by weight | of a compound of the formula (B1) and/or (B2) or of an active substance mixture consisting of a herbicidal active substance of the formula (A) and of a safener of the formula (B1) and/or (B2), |
| 5 parts by weight | sodium 2,2'-dinaphthylmethane-6,6'-disulfonate, |
| 2 parts by weight | oleoylmethyltaurine sodium salt, |
| 1 part by weight | polyvinyl alcohol, |
| 17 parts by weight | calcium carbonate and |
| 50 parts by weight | water | in a colloid mill, subsequently milling in a bead mill, and atomizing and drying the suspension obtained in this way in a spraying tower using a single-component nozzle.

BIOLOGICAL EXAMPLES

Example 1

Various crop plants are grown in plastic pots with a diameter of 9 cm in a glasshouse to the stated stage and then treated with the particular herbicide or with a mixture of the herbicide and the safener by the post-emergence method. This entails the herbicide of the formula (A) and the compounds of the formula (B) being applied in the form of aqueous suspensions or emulsions with a water application rate which converts to 300 l/ha. 4 weeks after the treatment, the plants are assessed visually for every type of damage by the applied herbicides, taking particular account of the extent of persistent growth inhibition. The evaluation takes place in percentages (scale from 0 to 100%) compared with untreated controls.

The results of the tests show that various safeners according to the invention make it possible selectively to use the herbicides in crops such as wheat, barley and corn without this having an adverse effect on the herbicidal activity.

TABLE 1

Phytotoxicity of herbicide/safener combinations according to the invention in cereals

| Herbicide Type A | Safener Type B | Dose [g AS/ha] A + B | Phytotoxicity Wheat | Phytotoxicity Barley |
|---|---|---|---|---|
| A1 | — | 20 | 50 | 80 |
|  | — | 10 | 25 | 50 |
|  | B1-1 | 20 + 40 | 0 | 15 |
|  |  | 10 + 20 | 0 | 0 |
|  | B1-9 | 20 + 40 | 0 | 25 |
|  |  | 10 + 20 | 0 | 0 |
|  | B1-6 | 20 + 40 | 0 | 20 |
|  |  | 10 + 20 | 0 | 0 |
| A2 | — | 20 | 60 | 80 |
|  | — | 10 | 20 | 40 |
|  | B1-1 | 20 + 40 | 5 | 15 |
|  |  | 10 + 20 | 0 | 0 |
|  | B1-9 | 20 + 40 | 10 | 15 |
|  |  | 10 + 20 | 0 | 0 |
|  | B1-6 | 10 + 20 | 0 | 5 |
| A3 | — | 20 | 65 | 95 |
|  | — | 10 | 30 | 60 |
|  | B1-1 | 20 + 40 | 10 | 20 |
|  |  | 10 + 20 | 0 | 0 |
|  | B1-9 | 20 + 40 | 15 | 25 |
|  |  | 10 + 20 | 0 | 0 |
|  | B1-6 | 20 + 40 | 10 | 25 |
|  |  | 10 + 20 | 0 | 0 |
| A4 | — | 40 | 40 | 80 |
|  | — | 20 | 15 | 30 |
|  | B1-1 | 40 + 80 | 0 | 15 |
|  |  | 20 + 40 | 0 | 0 |
|  | B1-9 | 40 + 80 | 0 | 10 |
|  |  | 20 + 40 | 0 | 0 |
|  | B1-6 | 40 + 80 | 0 | 25 |
|  |  | 20 + 40 | 0 | 0 |
| A5 | — | 40 | 20 | 50 |
|  | — | 20 | 5 | 25 |
|  | B1-1 | 40 + 80 | 0 | 0 |
|  |  | 20 + 40 | 0 | 0 |
|  | B1-9 | 40 + 80 | 0 | 0 |
|  |  | 20 + 40 | 0 | 0 |
|  | B1-6 | 40 + 80 | 0 | 5 |
|  |  | 20 + 40 | 0 | 0 |
| A6 | — | 40 | 40 | 85 |
|  | — | 20 | 15 | 30 |
|  | B1-1 | 40 + 80 | 0 | 20 |
|  |  | 20 + 40 | 0 | 0 |
|  | B1-9 | 40 + 80 | 0 | 5 |
|  |  | 20 + 40 | 0 | 0 |
|  | B1-6 | 40 + 80 | 0 | 20 |
|  |  | 20 + 40 | 0 | 0 |
| A10 |  | 25 | 30 | 55 |
|  |  | 12 | 25 | 15 |
|  |  | 6 | 15 | 5 |
|  | B1-1 | 25 + 12 | 0 | 5 |
|  |  | 12 + 6 | 0 | 0 |
|  |  | 6 + 3 | 0 | 0 |
| A11 |  | 25 | 45 | 45 |
|  |  | 12 | 20 | 25 |
|  |  | 6 | 5 | 10 |
|  | B1-1 | 25 + 12 | 5 | 10 |
|  |  | 12 + 6 | 0 | 0 |
|  |  | 6 + 3 | 0 | 0 |
|  | B1-9 | 25 + 12 | 10 | 15 |
|  |  | 12 + 6 | 0 | 5 |
|  |  | 6 + 3 | 0 | 0 |
| A12 |  | 25 | 10 | 25 |
|  |  | 12 | 10 | 15 |
|  |  | 6 | 5 | 8 |
|  | B1-1 | 25 + 12 | 0 | 5 |
|  |  | 12 + 6 | 0 | 0 |
|  |  | 6 + 3 | 0 | 0 |

Conditions: Application takes place at the initial stage of tillering of wheat and barley

TABLE 2

Herbicidal activity on grasses

| Herbicide Type A | Safener Type B | Dose [g AS/ha] A + B | % effect on ALMY | APSP | AVFA | POAN |
|---|---|---|---|---|---|---|
| A5 | — | 40 | 100 | 100 | 100 | 100 |
|  |  | 20 | 99 | 100 | 99 | 100 |
|  |  | 10 | 95 | 98 | 85 | 98 |
|  | B1-9 | 40 + 80 | 100 | 100 | 100 | 100 |
|  |  | 20 + 40 | 98 | 100 | 100 | 100 |
|  |  | 10 + 20 | 95 | 95 | 90 | 95 |
|  | B1-1 | 40 + 80 | 100 | 100 | 100 | 100 |
|  |  | 20 + 40 | 100 | 99 | 100 | 100 |
|  |  | 10 + 20 | 90 | 99 | 80 | 98 |
|  | B1-6 | 40 + 80 | 100 | 100 | 100 | 100 |
|  |  | 20 + 40 | 100 | 100 | 98 | 99 |
|  |  | 10 + 20 | 95 | 95 | 80 | 95 |
| A6 | — | 40 | 100 | 100 | 100 | 100 |
|  |  | 20 | 100 | 100 | 90 | 100 |
|  |  | 10 | 99 | 99 | 80 | 99 |
|  | B1-9 | 40 + 80 | 100 | 100 | 100 | 100 |
|  |  | 20 + 40 | 100 | 100 | 95 | 100 |
|  |  | 10 + 20 | 100 | 98 | 95 | 100 |
|  | B1-1 | 40 + 80 | 100 | 100 | 100 | 100 |
|  |  | 20 + 40 | 100 | 100 | 95 | 100 |
|  |  | 10 + 20 | 95 | 95 | 80 | 95 |
|  | B1-6 | 40 + 80 | 100 | 100 | 100 | 100 |
|  |  | 20 + 40 | 100 | 100 | 90 | 100 |
|  |  | 10 + 20 | 95 | 100 | 80 | 100 |
| A10 | — | 25 | 100 | 99 | 90 | 100 |
|  |  | 12 | 100 | 97 | 85 | 99 |
|  |  | 6 | 98 | 80 | 75 | 85 |
|  | B1-1 | 25 + 12 | 100 | 100 | 95 | 100 |
|  |  | 12 + 6 | 99 | 98 | 85 | 100 |
|  |  | 6 + 3 | 97 | 85 | 75 | 90 |
| A11 | — | 25 | 100 | 100 | 95 | 100 |
|  |  | 12 | 98 | 95 | 90 | 100 |
|  |  | 6 | 95 | 85 | 70 | 90 |
|  | B1-1 | 25 + 12 | 100 | 100 | 95 | 100 |
|  |  | 12 + 6 | 99 | 98 | 92 | 100 |
|  |  | 6 + 3 | 93 | 88 | 75 | 93 |
|  | B1-9 | 25 + 12 | 100 | 100 | 98 | 100 |
|  |  | 12 + 6 | 98 | 97 | 92 | 100 |
|  |  | 6 + 3 | 93 | 90 | 75 | 95 |
| A12 |  | 25 | 99 | 98 | 90 | 99 |
|  |  | 12 | 98 | 95 | 85 | 92 |
|  |  | 6 | 95 | 85 | 75 | 85 |
|  | B1-1 | 25 + 12 | 100 | 100 | 95 | 100 |
|  |  | 12 + 6 | 97 | 99 | 85 | 90 |
|  |  | 6 + 3 | 96 | 90 | 70 | 85 |

Stage of the grasses on application: 4-leaf stage

TABLE 3

Effect and selectivity in corn

| Herbicide A (+ safener B) | Dose [g AS/ha] | Phytotoxicity or herbicidal effect in % | | | |
|---|---|---|---|---|---|
| | | Corn | AVFA | ECCG | SOHA |
| A7 | 100 | 60 | 100 | 90 | 95 |
| | 50 | 40 | 100 | 80 | 90 |
| | 25 | 25 | 100 | 60 | 90 |
| A7 + B1-9 | 100 + 100 | 15 | 100 | 95 | 100 |
| | 50 + 50 | 0 | 100 | 80 | 95 |
| | 25 + 25 | 0 | 100 | 60 | 90 |
| A7 + B1-11 | 100 + 100 | 10 | 100 | 90 | 100 |
| | 50 + 50 | 0 | 100 | 90 | 90 |
| | 25 + 25 | 0 | 100 | 60 | 80 |
| A7 + B1-10 | 100 + 100 | 10 | 100 | 90 | 90 |
| | 50 + 50 | 0 | 100 | 90 | 90 |
| | 25 + 25 | 0 | 100 | 70 | 80 |
| A8 + B1-9 | 100 | 25 | — | — | — |
| | 50 | 10 | 100 | 100 | 98 |
| | 25 | 0 | 95 | 98 | 95 |
| A8 + B1-9 | 100 + 50 | 0 | — | — | — |
| | 50 + 25 | 0 | 100 | 100 | 100 |
| | 25 + 12 | 0 | 97 | 99 | 95 |
| A8 + B1-11 | 100 + 50 | 0 | — | — | — |
| | 50 + 25 | 0 | — | 100 | 100 |
| | 25 + 12 | 0 | — | 98 | 95 |
| A9 | 100 | 35 | — | — | — |
| | 50 | 15 | — | 100 | 100 |
| | 25 | 0 | — | 99 | 98 |
| A9 + B1-9 | 100 + 50 | 10 | — | — | — |
| | 50 + 25 | 0 | — | 100 | 100 |
| | 25 + 12 | 0 | — | 99 | 95 |
| A9 + B1-11 | 100 + 50 | 10 | — | — | — |
| | 50 + 25 | 0 | — | 99 | 99 |
| | 25 + 12 | 0 | — | 95 | 98 |
| A13 | 100 | 30 | — | — | — |
| | 50 | 20 | 95 | 100 | 97 |
| | 25 | 10 | 90 | 99 | 90 |
| A13 + B1-9 | 100 + 50 | 5 | — | — | — |
| | 50 + 25 | 0 | 98 | 100 | 98 |
| | 25 + 12 | 0 | 90 | 100 | 90 |

Stage: Corn - 4 leaves
AVFA - 3 leaves
ECCG: start of tillering (i.e. 4 to 5 leaves)
SOHA: 3 leaves Abbreviations in Tables 1 to 3:
g AS/ha=Application rate in grams of active substance per hectare
ALMY=*Alopecurus myosuroides*
APSP=*Apera spica-venti*
AVFA=*Avena fatua*
POAN=*Poa annua*
ECCG=*Echinochloa crus-galli*
SOHA=*Sorghum halepense*

(Continuation of Abbreviations in Tables 1 to 3)
A1=N-(4,6-Dimethoxypyrimidin-2-ylaminocarbonyl)-2-methoxycarbonyl-5-acetylaminobenzenesulfonamide
A2=N-(4,6-Dimethoxypyrimidin-2-ylaminocarbonyl)-2-methoxycarbonyl-5-(N-formyl-N-methylamino-methyl)benzenesulfonamide sodium salt
A3=N-(4,6-Dimethoxypyrimidin-2-ylaminocarbonyl)-2-methoxycarbonyl-5-acetylaminobenzenesulfonamide sodium salt
A4=N-(4,6-Dimethoxypyrimidin-2-ylaminocarbonyl)-2-methoxycarbonyl-5-(N-methyl-N-propionylamino)-benzenesulfonamide sodium salt
A5=N-(4,6-Dimethoxypyrimidin-2-ylaminocarbonyl)-2-methoxycarbonyl-5-(N-isopropionylmethylamino)-benzenesulfonamide sodium salt
A6=N-(4,6-Dimethoxypyrimidin-2-ylaminocarbonyl)-2-methoxycarbonyl-5-(N-methoxycarbonylaminomethyl) benzenesulfonamide sodium salt
A7=N-(4,6-Dimethoxypyrimidin-2-ylaminocarbonyl)-2-(N,N-dimethylaminocarbonyl)-5-(N-methoxycarbonylamino)benzenesulfonamide sodium salt
A8=N-(4,6-Dimethoxypyrimidin-2-ylaminocarbonyl)-2-(N,N-dimethylaminocarbonyl)-5-(N-formylamino)-benzenesulfonamide
A9=N-(4,6-Dimethoxypyrimidin-2-ylaminocarbonyl)-2-(N,N-dimethylaminocarbonyl)-5-(N-propionylamino)benzenesulfonamide sodium salt
A10=N-(4,6-Dimethoxypyrimidin-2-ylaminocarbonyl)-2-(methoxycarbonyl-5-(N-methylsulfonylaminomethyl) benzenesulfonamide sodium salt
A11=N-(4,6-Dimethoxypyrimidin-2-ylaminocarbonyl)-2-(methoxycarbonyl-5-(N-methoxycarbonylaminomethyl) benzenesulfonamide sodium salt
A12=N-(4,6-Dimethoxypyrimidin-2-ylaminocarbonyl)-2-(methoxycarbonyl-5-(N-methylsulfonyl-N-methyl-aminomethyl)benzenesulfonamide
A13=N-(4,6-Dimethoxypyrimidin-2-ylaminocarbonyl)-2-(N,N-dimethylaminocarbonyl)-5-(N-methoxycarbonylamino)benzenesulfonamide
B1-1=Ethyl 1-(2,4-dichlorophenyl)-5-(ethoxycarbonyl)-5-methyl-2-pyrazoline-3-carboxylate
B1-6=Ethyl 1-(2,4-dichlorophenyl)-5-(trichloromethyl-(1H)-1,2,4-triazole-3-carboxylate
B1-9=Ethyl 5,5-diphenyl-2-isoxazoline-3-carboxylate
B1-10=n-Propyl 5,5-diphenyl-2-isoxazoline-3-carboxylate
B1-11=Ethyl 5-(4-fluorophenyl)-5-phenyl-2-isoxazoline-3-carboxylate

The invention claimed is:

1. A herbicide/safener combination which comprises:
   A) at least one herbicidal active substance or a salt thereof, which is a substituted phenylsulfonylurea of the formula (A)

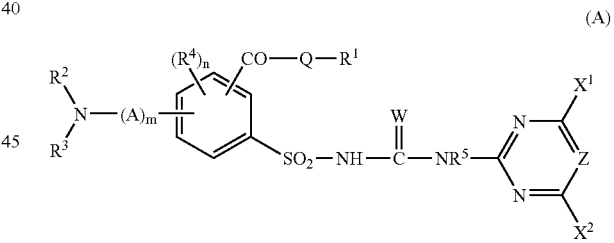

in which
W is O,
A is —CH$_2$—,
Q is O, or NR$^6$,
m is 0 or 1,
n is 0, 1, 2 or 3,
R$^1$ is H, unsubstituted or substituted (C$_1$–C$_6$)alkyl, unsubstituted or substituted (C$_2$–C$_6$)alkenyl, unsubstituted or substituted (C$_1$–C$_6$)alkynyl, or unsubstituted or substituted (C$_3$–C$_6$)cycloalkyl,
R$^2$ is H, OH, (C$_1$–C$_6$)alkyl, (C$_2$–C$_6$)alkenyl, (C$_2$–C$_6$)alkynyl, (C$_1$–C$_6$)alkoxy, (C$_2$–C$_6$)alkenyloxy, (C$_2$–C$_6$)alkylnyloxy, (C$_3$–C$_7$)cycloalkyl, or (C$_3$–C$_7$)cycloalkoxy,
R$^3$ is —C(O)—R$^{11}$ or —S(O$_2$)—R$^{21}$,
R$^4$ is halogen, CN, NO$_2$, (C$_1$–C$_4$)alkyl, (C$_1$–C$_4$)-alkoxy, [(C$_1$–C$_4$)alkyl]carbonyl, [(C$_1$–C$_4$)alkoxy]

carbonyl, each of the four last-mentioned radicals being unsubstituted or substituted, $R^5$ is H, $(C_1-C_5)$alkyl or $(C_1-C_4)$alkoxy, $R^6$ is H, $(C_1-C_4)$alkyl, $(C_3-C_4)$alkenyl, $(C_3-C_4)$alkynyl, each of the three last-mentioned radicals being unsubstituted or substituted by one or more radicals from the group consisting of halogen, $(C_1-C_4)$alkyl, $(C_1-C_4)$alkoxy and $(C_1-C_4)$alkylthio, or is $(C_1-C_4)$alkoxy or OH, $X^1$, $X^2$ are, independently of one another, H, halogen, $(C_1-C_6)$alkyl, $(C_2-C_6)$alkenyl, $(C_2-C_6)$alkynyl, $(C_3-C_7)$cycloalkyl, $(C_1-C_6)$alkoxy, $(C_2-C_6)$alkenyloxy, $(C_2-C_6)$alkynyloxy, $(C_1-C_6)$alkylthio, mono- or di-$[(C_1-C_4)$alkyl]-amino, each of the ten last-mentioned radicals being unsubstituted or substituted by one or more radicals from the group consisting of halogen, $(C_1-C_4)$alkoxy, $(C_1-C_4)$haloalkoxy and $(C_1-C_4)$alkylthio, Z is CH, $R^{11}$ is H, $(C_1-C_6)$alkyl, $(C_2-C_6)$alkenyl, or $(C_2-C_6)$alkynyl, and $R^{21}$ is $(C_1-C_6)$alkyl, $(C_2-C_6)$alkenyl or $(C_2-C_6)$alkynyl; and B) which is at least one safener from the group of compounds of the formulae (B1)

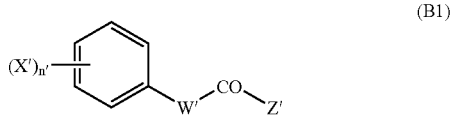

in which

X' is hydrogen, halogen, $(C_1-C_4)$alkyl, $(C_1-C_4)$alkoxy, nitro or $(C_1-C_4)$haloalkyl, Z' is $OR^7$, $SR^7$ or $NR^7R^8$ or is a saturated or unsaturated 3- to 7-membered heterocycle which has at least one nitrogen atom and up to 3 hetero atoms, is linked via the nitrogen atom to the carbonyl group in (B1) and is unsubstituted or substituted by radicals from the group consisting of $(C_1-C_4)$alkyl, optionally substituted phenyl, $R^7$ is hydrogen or an unsubstituted or substituted aliphatic hydrocarbon radical, $R^8$ is hydrogen, $(C_1-C_6)$alkyl, $(C_1-C_6)$alkoxy or optionally substituted phenyl, n' is an integer from 1 to 5, W' has the formula:

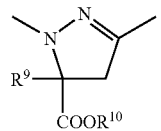

or ethyl 5,5-diphenyl-2-isoxazoline-3-carboxylate (B1-9).

2. A herbicide/safener combination as claimed in claim 1, which is formulated in the form of a composition (herbicidal composition) and contains 0.1 to 95% by weight of active substances (A) and (B) and 1 to 99.9% by weight of customary formulating agents.

3. A herbicide/safener combination as claimed in claim 1, which contains the active substances A and B in the ratio of from 1:100 to 100:1 by weight.

4. A method for protecting crop plants from phytotoxic side effects of herbicides A), which comprises applying an effective amount of safener B) before, after or at the same time as herbicide A to the plants, plant parts, plant seeds or the growing area, where the combination of herbicide A) and safener B) is as defined in claim 1.

5. The method as claimed in claim 4, wherein the crop plants are cereal plants, rice plants or corn plants.

6. The method as claimed in claim 4, wherein the herbicides A are applied at an application rate of 0.001 to 10 kg/ha active substance and a safener:herbicide ratio by weight of from 1:100 to 100:1.

7. The herbicide/safener combination as claimed in claim 1, wherein the herbicide is selected from the group consisting of N-(4,6-dimethoxypyrimidin-2-ylaminocarbonyl)-2-methoxycarbonyl-5-(N-isopropionylmethylamino)-benzenesulfonamide sodium salt (A5);

N-(4,6-dimethoxypyrimidin-2-ylaminocarbonyl)-2-methoxycarbonyl-5-(N-methoxycarbonylamino-methyl)benzenesulfonamide sodium salt (A6);

N-(4,6-dimethoxypyrimidin-2-ylaminocarbonyl)-2-(N,N-dimethylaminocarbonyl)-5-(N-methoxycarbonylamino)benzenesulfonamide sodium salt (A7);

N-(4,6-dimethoxypyrimidin-2-ylaminocarbonyl)-2-(N,N-dimethylaminocarbonyl)-5-(N-formylamino)-benzenesulfonamide (A8);

N-(4,6-dimethoxypyrimidin-2-ylaminocarbonyl)-2-(N,N-dimethylaminocarbonyl)-5-(N-propionylamino)-benzenesulfonamide sodium salt (A9);

N-(4,6-dimethoxypyrimidin-2-ylaminocarbonyl)-2-(methoxycarbonyl-5-(N-methylsulfonylaminomethyl)benzenesulfonamide sodium salt (A10); and N-(4,6-dimethoxypyrimidin-2-ylaminocarbonyl)-2-(N,N-dimethylaminocarbonyl)-5-(N-methoxycarbonylamino)benzenesulfonamide (A13);

and the safener is selected from the group consisting of ethyl 1-(2,4-dichlorophenyl)-5-(ethoxycarbonyl)-5-methyl-2-pyrazoline-3-carboxylate (B1-1) and ethyl 5,5-diphenyl-2-isoxazoline-3-carboxylate (B1-9).

8. A herbicide/safener combination as claimed in claim 7, wherein the herbicide is selected from the group consisting of N-(4,6-dimethoxypyrimidin-2-ylaminocarbonyl)-2-(N,N-dimethylaminocarbonyl)-5-(N-formylamino)-benzenesulfonamide (A8) and N-(4,6-dimethoxypyrimidin-2-ylaminocarbonyl)-2-(methoxycarbonyl-5-(N-methylsulfonylaminomethyl)benzenesulfonamide sodium salt (A10); and the safener is selected from the group consisting of ethyl 1-(2,4-dichlorophenyl)-5-(ethoxycarbonyl)-5-methyl-2-pyrazoline-3-carboxylate (B1-1) and ethyl 5,5-diphenyl-2-isoxazoline-3-carboxylate (B1-9).

9. A herbicide/safener combination as claimed in claim 7, wherein the herbicide is N-(4,6-dimethoxypyrimidin-2-ylaminocarbonyl)-2-methoxycarbonyl-5-(N-isopropionylmethylamino)-benzenesulfonamide sodium salt (A5) and the safener is ethyl 1-(2,4-dichlorophenyl)-5-(ethoxycarbonyl)-5-methyl-2-pyrazoline-3-carboxylate (B1-1).

10. A herbicide/safener combination as claimed in claim 7, wherein the herbicide is N-(4,6-dimethoxypyrimidin-2-ylaminocarbonyl)-2-methoxycarbonyl-5-(N-methoxycarbonylamino-methyl)benzenesulfonamide sodium salt (A6) and the safener is ethyl 1-(2,4-dichlorophenyl)-5-(ethoxycarbonyl)-5-methyl-2-pyrazoline-3-carboxylate (B1-1).

11. A herbicide/safener combination as claimed in claim 7, wherein the herbicide is N-(4,6-dimethoxypyrimidin-2-ylaminocarbonyl)-2-(N,N-dimethylaminocarbonyl)-5-(N- methoxycarbonylamino)benzenesulfonamide sodium salt (A7) and the safener is ethyl 5,5-diphenyl-2-isoxazoline-3-carboxylate (B1-9).

12. A herbicide/safener combination as claimed in claim 7, wherein the herbicide is N-(4,6-dimethoxypyrimidin-2-ylaminocarbonyl)-2-(N,N-dimethylaminocarbonyl)-5-(N-propionylamino)-benzenesulfonamide sodium salt (A9) and the safener is ethyl 5,5-diphenyl-2-isoxazoline-3-carboxylate (B1-9).

13. A herbicide/safener combination as claimed in claim 7, wherein the herbicide is n-propyl 5,5-diphenyl-2-N-(4,6-dimethoxypyrimidin-2-ylaminocarbonyl)-2-(N,N-dimethylaminocarbonyl)-5-(N-methoxycarbonylamino)benzenesulfonamide (A13) and the safener is ethyl 5,5-diphenyl-2-isoxazoline-3-carboxylate (B1-9).

14. A herbicide/safener combination as claimed in claim 1, wherein
W is O,
A is —CH$_2$—,
Q is 0,
m is 0 or 1,
n is 0,
$R^1$ is H or unsubstituted $(C_1-C_6)$alkyl,
$R^2$ is H or $(C_1-C_6)$alkyl,
$R^3$ is —C(O)—$R^{11}$,
$R^5$ is H or $(C_1-C_5)$alkyl,
$X^1$, $X^2$ are, independently of one another, H, halogen, $(C_1-C_6)$alkyl, or $(C_1-C_6)$alkoxy,
Z is CH; and
$R^{11}$ is H or $(C_1-C_6)$alkyl.

15. A herbicide/safener combination as claimed in claim 1, wherein, in the formula (B1),
$R^7$ is hydrogen, $(C_1-C_{18})$alkyl, $(C_3-C_{12})$cycloalkyl, $(C_2-C_8)$alkenyl or $(C_2-C_8)$alkynyl, where the above C-containing radicals are unsubstituted or substituted one or more times, by identical or different radicals from the group consisting of halogen, hydroxyl, $(C_1-C_8)$alkoxy, $(C_1-C_8)$alkylmercapto, $(C_2-C_8)$alkenylmercapto, $(C_2-C_8)$alkynylmercapto, $(C_2-C_8)$alkenyloxy, $(C_2-C_8)$alkynyloxy, $(C_3-C_7)$cycloalkyl, $(C_3-C_7)$cycloalkoxy, cyano, mono- and di-$(C_1-C_4$-alkyl)amino, carboxyl, $(C_1-C_8)$alkoxycarbonyl, $(C_2-C_8)$alkenyloxycarbonyl, $(C_1-C_8)$alkyl mercaptocarbonyl, $(C_2-C_8)$alkynyloxycarbonyl, $(C_1-C_8)$alkylcarbonyl, $(C_2-C_8)$alkenylcarbonyl, $(C_2-C_8)$alkynylcarbonyl, 1-(hydroxyimino)-$(C_1-C_6)$alkyl, 1-[$(C_1-C_4)$alkylimino]-$(C_1-C_4)$alkyl, 1-[$(C_1-C_4)$alkoxyimino]-$(C_1-C_6)$alkyl, $(C_1-C_8)$alkylcarbonylamino, $(C_2-C_8)$alkenylcarbonylamino, $(C_2-C_8)$alkynylcarbonylamino, aminocarbonyl, $(C_1-C_8)$alkylaminocarbonyl, di-$(C_1-C_6)$alkylaminocarbonyl, $(C_2-C_6)$alkenylaminocarbonyl, $(C_2-C_6)$alkynylaminocarbonyl, $(C_1-C_8)$alkoxycarbonylamino, $(C_1-C_8)$alkylaminocarbonylamino, $(C_1-C_6)$alkylcarbonyloxy, which is unsubstituted or substituted by halogen, nitro, $(C_1-C_4)$alkoxy or optionally substituted phenyl, or is $(C_2-C_6)$alkenylcarbonyloxy, $(C_2-C_6)$alkynylcarbonyloxy, $(C_1-C_8)$alkylsulfonyl, phenyl, phenyl-$(C_1-C_6)$alkoxy, phenyl-$(C_1-C_6)$alkoxycarbonyl, phenoxy, phenoxy-$(C_1-C_6)$alkoxy, phenoxy-$(C_1-C_6)$alkoxycarbonyl, phenylcarbonyloxy, phenylcarbonylamino, phenyl-$(C_1-C_6)$alkylcarbonylamino, where the 9 last-mentioned radicals are unsubstituted or substituted one or more times, in the phenyl ring by identical or different radicals from the group consisting of halogen, $(C_1-C_4)$alkyl, $(C_1-C_4)$alkoxy, $(C_1-C_4)$haloalkyl, $(C_1-C_4)$haloalkoxy and nitro, and radicals of the formulae —SiR'$_3$, —O—SiR'$_3$, R'$_3$Si— $(C_1-C_8)$alkoxy, —CO—O—NR'$_2$, —O—N=CR'$_2$, —N=CR'$_2$, —NR'$_2$, —O—NR'$_2$, —CH(OR')$_2$, —O—(CH$_2$)$_x$—CH(OR')$_2$, —CR'''(OR')$_2$ and —O—(CH$_2$)$_x$—CR'''(OR'')$_2$, in which the R' in the said formulae are, independently of one another, hydrogen, $(C_1-C_4)$alkyl, phenyl which is unsubstituted or substituted one or more times by identical or different radicals from the group consisting of halogen, $(C_1-C_4)$alkyl, $(C_1-C_4)$alkoxy, $(C_1-C_4)$haloalkyl, $(C_1-C_4)$haloalkoxy and nitro, or pairwise are a $(C_2-C_6)$alkanediyl chain and x=0 to 6, and R'' is hydrogen or $(C_1-C_4)$alkyl, and a substituted alkoxy radical of the formula R''OCHR'''CH(OR'')—$(C_1-C_6)$alkoxy, in which the R'' are, independently of one another, $(C_1-C_4)$alkyl or together are $(C_1-C_6)$alkanediyl and R''' is hydrogen or $(C_1-C_4)$alkyl,
W' has the formula:

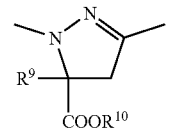

$R^9$ is hydrogen, $(C_1-C_8)$alkyl, $(C_1-C_8)$haloalkyl, $(C_3-C_{12})$cycloalkyl or optionally substituted phenyl,
$R^{10}$ is hydrogen, $(C_1-C_8)$alkyl, $(C_1-C_8)$haloalkyl, $(C_1-C_4)$alkoxy-$(C_1-C_4)$alkyl, $(C_1-C_6)$hydroxy-alkyl, $(C_3-C_{12})$cycloalkyl or tri-$(C_1-C_4)$alkyl-silyl.

16. A herbicide/safener combination as claimed in claim 1, wherein, in formula (A),
$R^1$ is $(C_1-C_6)$alkyl, $(C_2-C_6)$alkenyl, $(C_2-C_6)$alkynyl, $(C_3-C_6)$cycloalkyl each of the four last-mentioned radicals being unsubstituted or substituted by one or more radicals from the group consisting of halogen, CN, $(C_1-C_4)$alkoxy, $(C_1-C_4)$alkylthio, $(C_1-C_4)$haloalkoxy, mono-$(C_1-C_4$-alkyl)amino, di-$(C_1-C_4$-alkyl)amino, $(C_1-C_4)$alkylsulfonyl, $(C_1-C_4$-alkyl)aminocarbonyl, di-$(C_1-C_4$-alkyl)aminocarbonyl, phenyl and substituted phenyl, and
$R^2$ is H, OH, $(C_1-C_6)$alkyl, $(C_3-C_7)$cycloalkyl, $(C_2-C_6)$alkenyl, $(C_2-C_6)$alkynyl, $(C_1-C_6)$alkoxy, $(C_3-C_7)$cycloalkoxy, $(C_2-C_6)$alkenyloxy, $(C_2-C_6)$alkynyloxy, the eight last-mentioned radicals being unsubstituted or substituted by one or more radicals from the group consisting of $(C_1-C_4)$alkoxy, $(C_1-C_4)$ haloalkoxy, $(C_2-C_4)$alkenyloxy, $(C_2-C_4)$haloalkenyloxy, $(C_2-C_4)$alkynyloxy, $(C_2-C_4)$ haloalkynyloxy, $(C_1-C_4)$alkylthio, $(C_1-C_4)$haloalkylthio, halogen, OH, NH$_2$, mono- and di-[$(C_1-C_4)$alkyl]amino, CN, NO$_2$, CONH$_2$, CHO, [$(C_1-C_6)$alkyl]carbonyl, $(C_1-C_4)$alkylsulfonyl, [$(C_1-C_4)$alkoxy]carbonyl, mono- and di-[$(C_1-C_4)$alkyl]aminocarbonyl, and in the case of cyclic radicals also $(C_1-C_4)$alkyl and $(C_1-C_4)$haloalkyl.

17. A herbicide/safener combination as claimed in claim 1, wherein
$R^1$ is $(C_1-C_6)$alkyl, $(C_2-C_6)$alkenyl, $(C_2-C_6)$alkynyl, $(C_3-C_6)$cycloalkyl, each of the four last-mentioned radicals being unsubstituted or substituted by one or more radicals selected from the group consisting of F, Cl, Br, I, CN, OCH$_3$, OCF$_3$, N(CH$_3$)$_2$, SO$_2$CH$_3$, CO$_2$CH$_3$, CO$_2$N(CH$_3$)$_2$ and phenyl, $R^2$ is H, $(C_1-C_4)$alkyl, $(C_2-C_4)$alkenyl, $(C_2-C_4)$alkynyl, $(C_3-C_6)$cycloalkyl or $(C_1-C_4)$haloalkyl.

* * * * *